(12) United States Patent
Thomas Carazo et al.

(10) Patent No.: US 9,926,349 B2
(45) Date of Patent: Mar. 27, 2018

(54) CHIMERIC MOLECULE USEFUL IN IMMUNOTHERAPY FOR LEISHMANIASIS, WHICH INCLUDES A FRAGMENT OF THE PFR1 PROTEIN OF LEISHMANIA INFANTUM WITH SPECIFIC IMMUNODOMINANT EPITOPES

(75) Inventors: Maria del Carmen Thomas Carazo, Armilla (ES); Manuel Carlos López López, Armilla (ES); Darién Ledesma Arroyo, Armilla (ES)

(73) Assignee: Consejo Superior de Investigaciones Cientificas (CSIC), Madrid (ES)

( * ) Notice: Subject to any disclaimer, the term of this patent is extended or adjusted under 35 U.S.C. 154(b) by 153 days.

(21) Appl. No.: 14/234,075

(22) PCT Filed: Jul. 17, 2012

(86) PCT No.: PCT/ES2012/070541
§ 371 (c)(1),
(2), (4) Date: Jun. 12, 2014

(87) PCT Pub. No.: WO2013/011184
PCT Pub. Date: Jan. 24, 2013

(65) Prior Publication Data
US 2014/0286974 A1 Sep. 25, 2014

(30) Foreign Application Priority Data
Jul. 21, 2011 (ES) .................................. 201131257

(51) Int. Cl.
| | | |
|---|---|---|
| C07K 14/44 | (2006.01) | |
| A61K 39/00 | (2006.01) | |
| A61K 39/008 | (2006.01) | |
| C12Q 1/04 | (2006.01) | |
| C12Q 1/68 | (2018.01) | |

(52) U.S. Cl.
CPC ............ *C07K 14/44* (2013.01); *A61K 39/008* (2013.01); *C12Q 1/04* (2013.01); *C12Q 1/6893* (2013.01); *A61K 2039/53* (2013.01); *A61K 2039/6043* (2013.01)

(58) Field of Classification Search
None
See application file for complete search history.

(56) References Cited

U.S. PATENT DOCUMENTS

| | | | | |
|---|---|---|---|---|
| 7,888,135 B2 * | 2/2011 | Tarleton | ............... | A61K 39/005 436/518 |
| 8,329,411 B2 * | 12/2012 | Tarleton | ............... | G01N 33/569 435/7.1 |
| 8,900,598 B2 * | 12/2014 | de Baeremaecker Barros ............................ A61K 39/005 424/185.1 |
| 2010/0323909 A1 * | 12/2010 | Tarleton | ............... | G01N 33/569 506/9 |
| 2014/0286974 A1 * | 9/2014 | Thomas Carazo | .. | A61K 39/008 424/185.1 |

OTHER PUBLICATIONS

Waeger, F. et al. "Paraflagellar rod protein 1[Leishmania infantum]". Sep. 5, 2004. Genbank Database, NCBI, National Institutes of Health, Bethesda, MD, USA, GenBank AY023444, www.ncbi.nlm.nih.gov.*
Gadelha et al, Molecular & Biochemical Parasitology 136 (2004) 113-115.*
Kumar et al, J. Camel Practice and Research, 2013, 20/2:191-196.*
Bastin et al, Parasitology Today, 1996, 12/8:302-307.*
Dumonteil, Infection, Genetics and Evolution, 2009, 9:1075-1082.*
Maga et al, trends in Cell Biology, Oct. 1999, 9:409-413.*
Miller et al, Experimental Parasitology, 1996, 84:156-167.*
Portman et al, International J. Parasitology, 2010, 40:135-140.*
Luhrs et al, Vaccine, 2003, 21:3058-3069.*
Beard et al, J. Biological Chemistry, Oct. 25, 1992, 267/30:21656-21662.*
Maga et al, J. Cell Science, 1999, 112:2753-2763.*
Morell et al, Vaccine, 2006, 24:7046-7055.*
Nagill et al, International Immunopharmacology 11 (2011) 1464-1488.*
Jain et al, J. Immunological Methods, 2015, 422:1-12.*
Alcolea et al, Transcriptomocs throughout the life cycle of Leishmania infantum: High down-regulation rate in the amastigote stage. International J. Parasitology, 2010, 40/13:1497-1516.*
Rodgers et al, Genome Research, 2011, 21/12:2129-2142.*
Ivens et al, Science, 2005, 309(5733):436-442.*
Mishra et al, Euk. Cell, 2003, 2/5:1009-1017.*
Ledesma-Arroyo, D., "Identificacion de Epitopes CD8+ en la Proteina PFR1 de Leishmania Infantum y Determinacion de su Inmunogenicidad como Vacuna Plasmidica," Tesina de Licenciatura, Universidad de Granada, Dec. 17, 2010, 47 pages. (Includes Nondisclosure Agreement and Declarations.).
Alvar, J. et al., "Canine Leishmaniasis," Advanced Parasitology 57:1-88, 2004.
Asea, A., et al., "HSP70 Stimulates Cytoldne Production Through a CD14-Dependant Pathway, Demonstrating Its Dual Role as a Chaperone and Cytokine" Nature Medicine 6(4):435-442, Apr. 2000.

(Continued)

*Primary Examiner* — Nita M Minnifield
(74) *Attorney, Agent, or Firm* — Barry L. Davison; Davis Wright Tremaine LLP

(57) ABSTRACT

The present invention claims an isolated nucleotide sequence characterized by encoding the PFR1 protein of *Leishmania infantum* or a fragment thereof. This PFR1 protein or a fragment thereof comprises at least a selected immunodominant epitope between the following group: SEQ ID No: 1, SEQ ID No: 2, SEQ ID No: 3, SEQ ID No: 4, SEQ ID No: 5, SEQ ID No: 6, SEQ ID No: 7 and SEQ ID No: 8, where the immunodominant epitope is able to induce an antigen-specific T cell cytotoxic immune response in an animal, against the kinetoplastids causing the leishmaniasis disease. The immunodominant epitopes are cytotoxic T-lymphocyte activators and they present a high binding affinity for A2 type MHC Class I molecule.

4 Claims, 10 Drawing Sheets

(56) References Cited

OTHER PUBLICATIONS

Figure 1:
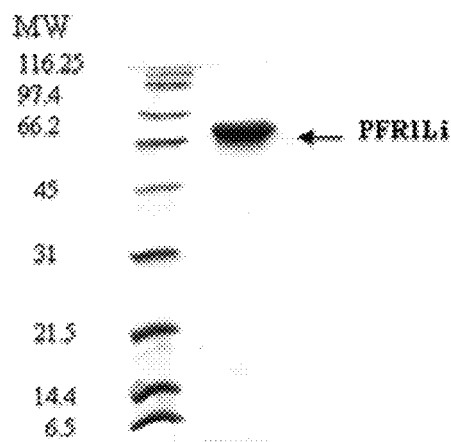

Badaro, R., et al., "Immunotherapy for Drug-Refractory Mucosal Leishmaniasis," Journal of Infectious Disease 194(8):1151-1159 Oct. 15 2006.

Basu, S., et al., "CD91 Is a Common Receptor for Heat Shock Proteins gp96, hsp90, hsp70, and Calreticulin," Immunity 14(3):303-313 Mar. 2001.

Buffet, P.A., et al., "Culture Microtitration: A Sensitive Method for Quantifying Leishmania infantum in Tissues of Infected Mice," Antimicrobial Agents and Chemotherapy 39(9):2167-2168, Sep. 1995.

Clark, A.K., et al., "Cloning and Expression Analysis of Two Novel Paraflagellar Rod Domain Genes Found in Trypanosoma cruzi," Parasitology Research 96(5):312-320, Jul. 2005.

Convit, J., et al., "Immunotherapy of American Cutaneous Leishmaniasis in Venezuela During the Period 1990-99," Transactions of the Royal Society of Tropical Medicine and Hygiene 97(4):469-472, Jul.-Aug. 2003.

DE Oliveira, C.I., et al., "Challenges and Perspectives in Vaccination Against Leishmaniasis," Parasitology International 58(4):319-324, Dec. 2009.

El-On, J., "Current Status and Perspectives of the Immunotherapy of Leishmaniasis;" The Israel Medical Association Journal 11(10):623-628, Oct. 2009.

Fouts, D.L., et al., "Evidence for Four Distinct Major Protein Components in the Paraflagellar Rod of Trypanosoma cruzi," The Journal of Biological Chemistry 273(34):21846-21855, Aug. 21, 1998.

Harmala, L.A.E., et al., "The Adjuvant Effects of Mycobacterium Tuberculosis Heat Shock Protein 70 Result From the Rapid and Prolonged Activation of Antigen-Specific CD8+ T Cells In Vivo," The Journal of Immunology 169(10):5622-5629, Nov. 15, 2002.

Kaur, T., et al., "Cocktail of gp63 and Hsp70 Induces Protection Against Leishmania Donovani in BALB/c Mice," Parasite Immunology 33(2):95-103, Feb. 2011.

Kedzierski, L., "Leishmaniasis Vaccine: Where Are We Today?," Journal of Global Infectious Diseases 2(2):177-185, 2010.

Kedzierski, L., et al., "Leishmania Vaccines: Progress and Problems," Parasitology, 133(Supplement S2):S87-S112, Oct. 2006.

Ledesma-Arroyo, D., "Identificacion de Epitopes CD8+ en la Proteina PFR1 de Leishmania Infantum y Determinacion de su Inmunogenicidad como Vacuna Plasmidica," Tesina de Licenciatura, Universidad de Granada, Dec. 17, 2010, pp. 1-27.

Marañón, C., et al., "HSP70 From Trypanosoma cruzi Is Endowed With Specific Cell Proliferation Potential Leading to Apoptosis," International Immunology 12(12):1685-1693, 2000.

Michailowsky, V., et al., "Humoral and Cellular Immune Responses to Trypanosoma cruzi-Derived Parafiagellar Rod Proteins in Patients With Chagas' Disease," Infection and Immunity 71(6):3165-3171, Jun. 2003.

Palatnik-De-Sousa, C.B., "Vaccines for Leishmaniasis in the Fore Coming 25 Years," Vaccine 26(14):1709-1724, Mar. 25, 2008.

Planelles, L., et al., "DNA Immunization With Trypanosoma Cruzi HSP70 Fused to the KMP11 Protein Elicits a Cytotoxic and Humoral Immune Response Against the Antigen and Leads to Protection," Infection and Immunity 69(10):6558-6563, Oct. 1, 2001.

Qazi, K.R., et al., "Microbial Heat Shock Protein 70 Stimulatory Properties Have Different TLR Requirements," Vaccine 25(6):1096-1103, Jan. 22, 2007.

Reis, A.B., et al., "Immunity to Leishmania and the Rational Search for Vaccines Against Canine Leishmaniasis," Trends in Parasitology 26(7):341-349, Jul. 2010.

Requena, J.M., et al., "Recent Advances in Vaccines for Leishmaniasis," Expert Opinion on Biological Therapy 4(9)1505-1517, 2004.

Saravia, N.G., et al., "Protective Immunogenicity of the Paraflagellar Rod Protein 2 of Leishmania Mexicana," Vaccine 23(8):984-995, Jan. 11, 2005.

Smith, D.F., et al., "Molecular Chaperones: Biology and Prospects for Pharmacological Intervention," Pharmacological Reviews 50(4):493-513, Dec. 1, 1998.

Srivastava, P., "Roles of Heat-Shock Proteins in Innate and Adaptive Immunity," Nature Reviews Immunology 2:185-194, Mar. 2002.

Thomas, M.C., et al., "Molecular Characterization of KMP11 From Trypanosoma cruzi: A Cytoskeleton-Associated Protein Regulated at the Translational Level," DNA and Cell Biology 19(1):47-57, Nov. 1, 2000.

Thomas, M.C., et al., "Plasticity of the Histone H2A Genes in a Brazilian and Six Colombian Strains of Trypanosoma cruzi," Acta Tropica 75(2):203-210, Mar. 25, 2000.

Tobian, A.A.R., et al., "Bacterial Heat Shock Proteins Enhance Class II MHC Antigen Processing and Presentation of Chaperoned Peptides to CD4+ T Cells," The Journal of Immunology 173(8):5130-5137, Oct. 15, 2004.

Wrightsman, R.A., and J.E. Manning, "Paraflagellar Rod Proteins Administered With Alum and IL-12 or Recombinant Adenovirus Expressing IL-12 Generates Antigen-Specific Responses and Protective Immunity in Mice Against Trypanosoma cruzi," Vaccine 18(14):1419-1427, Feb. 4, 2000.

Wrightsman, R.A., et al., "Paraflagellar Rod Protein-Specific CD8+ Cytotoxic T Lymphocytes Target Trypanosoma cruzi-Infected Host Cells," Parasite Immunology 24(8):401-412, Aug. 2002.

Wu, Y., et al., "Hsp70-Like Protein 1 Fusion Protein Enhances Induction of Carcinoembryonic Antigen-Specific CD8+ CTL Response by Dendritic Cell Vaccine," Cancer Research 65(11):4947-4954, Jun. 1, 2005.

International Search Report dated Dec. 5, 2012, issued in International Patent Application No. PCT/ES2012/070541, filed Jul. 17, 2012, 12 pages.

Miller, M.J., et al., "Protection of Mice Against Trypanosoma cruzi by Immunization With Paraflagellar Rod Proteins Requires T Cell, But Not B Cell, Function," The Journal of Immunology 158(11):5330-5337, Jun. 1, 1997.

\* cited by examiner

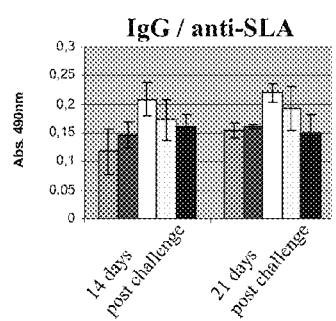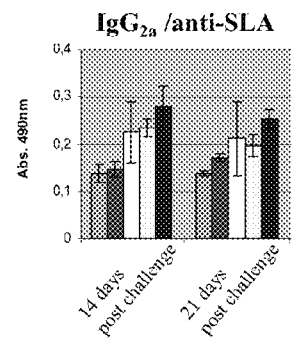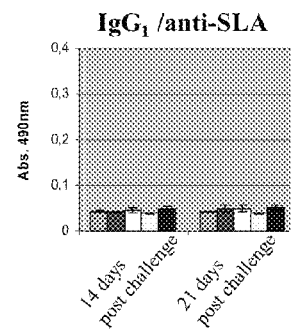
Fig. 5A          Fig. 5B          Fig. 5C
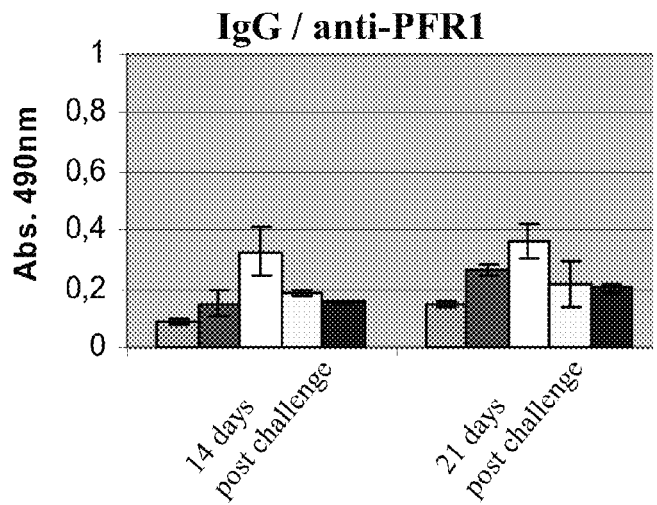
Fig. 5D

| Peptide | Saline Solution | pCMV4 PFR1 | pCMV4 PFR1Hsp70 |
|---|---|---|---|
| 1864 | - | - | - |
| 1865 | - | - | - |
| 1866 | - | - | 430 |
| 1868 | - | - | 386 |
| 1869 | - | - | 452 |
| 1871 | - | 164 | - |
| 1872 | - | - | 230 |
| 1873 | - | - | 442 |

Fig. 10

| Peptide | Non infected | Infected |
|---|---|---|
| 1864 | - | 266 |
| 1865 | - | - |
| 1866 | - | - |
| 1868 | - | - |
| 1869 | - | - |
| 1871 | - | 376 |
| 1872 | - | 390 |
| 1873 | - | 466 |

Fig. 11

| Peptide | Non infected | Infected |
|---|---|---|
| 1864 | - | - |
| 1865 | - | - |
| 1866 | - | - |
| 1868 | - | - |
| 1869 | - | - |
| 1871 | - | 104 |
| 1872 | - | 87 |
| 1873 | 83 | 98 |

Fig. 12

Nonamers:

| Position | SEQUENCE | SYFPEITHI | RANKPEP | BIMAS (min) |
|---|---|---|---|---|
| 165 (1868) | K M M E D I M N A | 20 | 54% | 438 |
| 186 | Q M Q T Q L A Q L | 24 | 64% | 35 |
| 204 (1869) | A M H D G E T Q V | 23 | 59% | 206 |
| 222 (1871) | Q L Q E R L I E L | 28 | 68% | 201 |
| 229 | E L L K D K F G L | 20 | 24% | 34 |
| 395 | L V S E G C A G V | 21 | 29% | 42 |
| 431 (1872) | M L Y L T L G S L | 27 | 64% | 35 |
| 532 | V L T R R S K M V | 19 | 62% | 118 |
| 538 (1873) | K M V E Y K S H L | 22 | 57% | 222 |

Decamers:

| Position | SEQUENCE | SYFPEITHI | RANKPEP | BIMAS (min) |
|---|---|---|---|---|
| 1 | M M T P E D A T G L | 20 | 23% | 26 |
| 103 (1864) | F M D I I G V K K V | 24 | 25% | 213 |
| 130 | Q L I D N S I A K M | 25 | N.D. | 47 |
| 150 (1865) | Q L D A T Q L A Q V | 26 | 31% | 64 |
| 165 | K M M E D I M N A T | 18 | 22% | 657 |
| 222 | Q L Q E R L I E L L | 26 | 29% | 99 |
| 373 (1866) | K L L E L T V Y N C | 20 | N.D. | 606 |

Fig. 13

| Peptide | Saline Solution | pCIVM4 436aaPFR1 | pCIVM4 436aaPFR1Hsp70 |
|---|---|---|---|
| 1864 | - | - | - |
| 1865 | - | - | - |
| 1866 | - | - | 419 |
| 1868 | - | - | 401 |
| 1869 | - | - | 466 |
| 1871 | - | 171 | - |
| 1872 | - | - | 233 |
| 1873 | - | - | 418 |

SEQUENCE LISTING

<160> NUMBER OF SEQ ID NOS: 13

<210> SEQ ID NO 1
<211> LENGTH: 10
<212> TYPE: PRT
<213> ORGANISM: Leishmania infantum
<220> FEATURE:
<221> NAME/KEY: SOURCE
<222> LOCATION: 1..10
<223> OTHER INFORMATION: /mol_type="protein"
      /organism="Leishmania infantum"
<220> FEATURE:
<221> NAME/KEY: PEPTIDE
<222> LOCATION: 1..10
<223> OTHER INFORMATION: "Sequence 1866 corresponds to Li PFR1 protein
      (amino acids 103-113)"
<220> FEATURE:
<221> NAME/KEY: PEPTIDE
<222> LOCATION: 1..10
<223> OTHER INFORMATION: "High affinity MCH class I, type A2 molecule
      immunodominant epitope"

<400> SEQUENCE: 1

Phe Met Asp Ile Ile Gly Val Lys Lys Val
1               5                   10

<210> SEQ ID NO 2
<211> LENGTH: 10
<212> TYPE: PRT
<213> ORGANISM: Leishmania infantum
<220> FEATURE:
<221> NAME/KEY: SOURCE
<222> LOCATION: 1..10
<223> OTHER INFORMATION: /mol_type="protein"
      /organism="Leishmania infantum"
<220> FEATURE:
<221> NAME/KEY: PEPTIDE
<222> LOCATION: 1..10
<223> OTHER INFORMATION: "Sequence 1866 corresponds to Li PFR1 protein
      (amino acids 150-159)"
<220> FEATURE:
<221> NAME/KEY: PEPTIDE
<222> LOCATION: 1..10
<223> OTHER INFORMATION: "High affinity MCH class I, type A2 molecule
      immunodominant epitope"

<400> SEQUENCE: 2

Gln Leu Asp Ala Thr Gln Leu Ala Gln Val
1               5                   10

<210> SEQ ID NO 3
<211> LENGTH: 10
<212> TYPE: PRT
<213> ORGANISM: Leishmania infantum
<220> FEATURE:
<221> NAME/KEY: SOURCE
<222> LOCATION: 1..10
<223> OTHER INFORMATION: /mol_type="protein"
      /organism="Leishmania infantum"
<220> FEATURE:
<221> NAME/KEY: PEPTIDE
<222> LOCATION: 1..10
<223> OTHER INFORMATION: "Sequence 1866 corresponds to Li PFR1 protein
      (amino acids 373-382)"
<220> FEATURE:
<221> NAME/KEY: PEPTIDE
<222> LOCATION: 1..10
<223> OTHER INFORMATION: "High affinity MCH class I, type A2 molecule
      immunodominant epitope"
<220> FEATURE:
<221> NAME/KEY: PEPTIDE
<222> LOCATION: 1..10
<223> OTHER INFORMATION: "Cytotoxic T lymphocytes activator
      immunodominant epitope"

-continued

```
<400> SEQUENCE: 3

Lys Leu Leu Glu Leu Thr Val Tyr Asn Cys
1               5                   10

<210> SEQ ID NO 4
<211> LENGTH: 9
<212> TYPE: PRT
<213> ORGANISM: Leishmania infantum
<220> FEATURE:
<221> NAME/KEY: SOURCE
<222> LOCATION: 1..9
<223> OTHER INFORMATION: /mol_type="protein"
      /organism="Leishmania infantum"
<220> FEATURE:
<221> NAME/KEY: PEPTIDE
<222> LOCATION: 1..9
<223> OTHER INFORMATION: "Sequence 1868 corresponds to Li PFR1 protein
      (amino acids 165-173)"
<220> FEATURE:
<221> NAME/KEY: PEPTIDE
<222> LOCATION: 1..9
<223> OTHER INFORMATION: "High affinity MCH class I, type A2 molecule
      immunodominant epitope"
<220> FEATURE:
<221> NAME/KEY: PEPTIDE
<222> LOCATION: 1..9
<223> OTHER INFORMATION: "Cytotoxic T lymphocytes activator
      immunodominant epitope"

<400> SEQUENCE: 4

Lys Met Met Glu Asp Ile Met Asn Ala
1               5

<210> SEQ ID NO 5
<211> LENGTH: 9
<212> TYPE: PRT
<213> ORGANISM: Leishmania infantum
<220> FEATURE:
<221> NAME/KEY: SOURCE
<222> LOCATION: 1..9
<223> OTHER INFORMATION: /mol_type="protein"
      /organism="Leishmania infantum"
<220> FEATURE:
<221> NAME/KEY: PEPTIDE
<222> LOCATION: 1..9
<223> OTHER INFORMATION: "Sequence 1869 corresponds to Li PFR1 protein
      (amino acids 204-212)"
<220> FEATURE:
<221> NAME/KEY: PEPTIDE
<222> LOCATION: 1..9
<223> OTHER INFORMATION: "High affinity MCH class I, type A2 molecule
      immunodominant epitope"
<220> FEATURE:
<221> NAME/KEY: PEPTIDE
<222> LOCATION: 1..9
<223> OTHER INFORMATION: "Cytotoxic T lymphocytes activator
      immunodominant epitope"

<400> SEQUENCE: 5

Ala Met His Asp Gly Glu Thr Gln Val
1               5

<210> SEQ ID NO 6
<211> LENGTH: 9
<212> TYPE: PRT
<213> ORGANISM: Leishmania infantum
<220> FEATURE:
<221> NAME/KEY: SOURCE
<222> LOCATION: 1..9
<223> OTHER INFORMATION: /mol_type="protein"
      /organism="Leishmania infantum"
<220> FEATURE:
```

```
<221> NAME/KEY: PEPTIDE
<222> LOCATION: 1..9
<223> OTHER INFORMATION: "Sequence 1871 corresponds to Li PFR1 protein
      (amino acids 220-230)"
<220> FEATURE:
<221> NAME/KEY: PEPTIDE
<222> LOCATION: 1..9
<223> OTHER INFORMATION: "Cytotoxic T lymphocytes activator
      immunodominant epitope"
<220> FEATURE:
<221> NAME/KEY: PEPTIDE
<222> LOCATION: 1..9
<223> OTHER INFORMATION: "High affinity MCH class I, type A2 molecule
      immunodominant epitope"

<400> SEQUENCE: 6

Gln Leu Gln Glu Arg Leu Ile Glu Leu
1               5

<210> SEQ ID NO 7
<211> LENGTH: 9
<212> TYPE: PRT
<213> ORGANISM: Leishmania infantum
<220> FEATURE:
<221> NAME/KEY: SOURCE
<222> LOCATION: 1..9
<223> OTHER INFORMATION: /mol_type="protein"
      /organism="Leishmania infantum"
<220> FEATURE:
<221> NAME/KEY: PEPTIDE
<222> LOCATION: 1..9
<223> OTHER INFORMATION: "Sequence 1872 corresponds to Li PFR1 protein
      (amino acids 431-440)"
<220> FEATURE:
<221> NAME/KEY: PEPTIDE
<222> LOCATION: 1..9
<223> OTHER INFORMATION: "Cytotoxic T lymphocytes activator
      immunodominant epitope"
<220> FEATURE:
<221> NAME/KEY: PEPTIDE
<222> LOCATION: 1..9
<223> OTHER INFORMATION: "High affinity MCH class I, type A2 molecule
      immunodominant epitope"

<400> SEQUENCE: 7

Met Leu Tyr Leu Thr Leu Gly Ser Leu
1               5

<210> SEQ ID NO 8
<211> LENGTH: 9
<212> TYPE: PRT
<213> ORGANISM: Leishmania infantum
<220> FEATURE:
<221> NAME/KEY: SOURCE
<222> LOCATION: 1..9
<223> OTHER INFORMATION: /mol_type="protein"
      /organism="Leishmania infantum"
<220> FEATURE:
<221> NAME/KEY: PEPTIDE
<222> LOCATION: 1..9
<223> OTHER INFORMATION: "Sequence 1873 corresponds to Li PFR1 protein
      (amino acids 538-546)"
<220> FEATURE:
<221> NAME/KEY: PEPTIDE
<222> LOCATION: 1..9
<223> OTHER INFORMATION: "High affinity MCH class I, type A2 molecule
      immunodominant epitope"
<220> FEATURE:
<221> NAME/KEY: PEPTIDE
<222> LOCATION: 1..9
<223> OTHER INFORMATION: "Cytotoxic T lymphocytes activator
      immunodominant epitope"

<400> SEQUENCE: 8
```

Lys Met Val Glu Tyr Lys Ser His Leu
1               5

<210> SEQ ID NO 9
<211> LENGTH: 436
<212> TYPE: PRT
<213> ORGANISM: Leishmania infantum
<220> FEATURE:
<221> NAME/KEY: SOURCE
<222> LOCATION: 1..436
<223> OTHER INFORMATION: /mol_type="protein"
      /organism="Leishmania infantum"
<220> FEATURE:
<221> NAME/KEY: REGION
<222> LOCATION: 1..436
<223> OTHER INFORMATION: "PFR1 fragment aminoacids 160-595"
<220> FEATURE:
<221> NAME/KEY: PEPTIDE
<222> LOCATION: 6..14
<223> OTHER INFORMATION: "SEQ ID No: 4"
<220> FEATURE:
<221> NAME/KEY: PEPTIDE
<222> LOCATION: 45..53
<223> OTHER INFORMATION: "SEQ ID No: 5"
<220> FEATURE:
<221> NAME/KEY: PEPTIDE
<222> LOCATION: 63..71
<223> OTHER INFORMATION: "SEQ ID No: 6"
<220> FEATURE:
<221> NAME/KEY: PEPTIDE
<222> LOCATION: 214..223
<223> OTHER INFORMATION: "SEQ ID No: 3"
<220> FEATURE:
<221> NAME/KEY: PEPTIDE
<222> LOCATION: 272..280
<223> OTHER INFORMATION: "SEQ ID No: 7"
<220> FEATURE:
<221> NAME/KEY: PEPTIDE
<222> LOCATION: 379..387
<223> OTHER INFORMATION: "SEQ ID no: 8"

<400> SEQUENCE: 9

Pro Thr Arg Thr Val Lys Met Met Glu Asp Ile Met Asn Ala Thr Gln
1               5                   10                  15

Ile Gln Asn Ala Leu Ala Ser Thr Asp Asp Gln Met Gln Thr Gln Leu
            20                  25                  30

Ala Gln Leu Glu Lys Thr Asn Glu Ile Gln Asn Val Ala Met His Asp
        35                  40                  45

Gly Glu Thr Gln Val Ala Glu Glu Gln Met Trp Thr Lys Val Gln Leu
    50                  55                  60

Gln Glu Arg Leu Ile Glu Leu Leu Lys Asp Lys Phe Gly Leu Ile Gly
65                  70                  75                  80

Lys Cys Glu Glu Glu Asn Ala Gln Phe Lys Glu Ile Tyr Glu Val Gln
                85                  90                  95

Lys Gln Ala Asn Gln Glu Thr Ser Gln Met Lys Asp Ala Lys Arg Arg
            100                 105                 110

Leu Arg Gln Arg Cys Glu Thr Asp Leu Lys His Ile Gln Asp Ala Ile
        115                 120                 125

Gln Lys Ala Asp Leu Glu Asp Ala Glu Ala Val Lys Arg Tyr Pro Arg
    130                 135                 140

Asn Lys Glu Arg Ser Glu Arg Ala Ile Lys Glu Asn Glu Glu Met Gln
145                 150                 155                 160

Glu Glu Ala Trp Asn Lys Ile Gln Asp Leu Gly Arg Gln Leu Gln Asn
                165                 170                 175

Leu Gly Thr Asp Arg Phe Asp Glu Val Lys Arg Arg Ile Glu Glu Val
            180                 185                 190

-continued

```
Asp Arg Glu Glu Lys Arg Val Glu Asn Ala Gln Phe Leu Glu Ile
        195                 200                 205

Ala Ala Gln His Lys Lys Leu Leu Glu Leu Thr Val Tyr Asn Cys Asp
210                 215                 220

Leu Ala Met Arg Cys Thr Gly Leu Val Glu Glu Leu Val Ser Glu Gly
225                 230                 235                 240

Cys Ala Gly Val Lys Ala Arg Tyr Asp Lys Thr Asn Gln Asp Leu Ala
                245                 250                 255

Ala Leu Arg Leu Glu Val His Lys Glu His Leu Glu Tyr Phe Arg Met
                260                 265                 270

Leu Tyr Leu Thr Leu Gly Ser Leu Ile Tyr Lys Lys Glu Lys Arg Leu
        275                 280                 285

Glu Glu Ile Asp Arg Asn Ile Arg Leu Ala His Ile Gln Leu Glu Phe
        290                 295                 300

Cys Val Glu Thr Phe Asp Pro Asn Ala Lys Lys His Ala Asp Met Lys
305                 310                 315                 320

Lys Glu Leu Tyr Arg Leu Arg Gln Gly Val Glu Glu Leu Ala Met
                325                 330                 335

Leu Lys Glu Lys Gln Ala Ala Ala Leu Asp Asp Phe Lys Glu Ser Glu
                340                 345                 350

Glu Ala Leu Asp Ala Ala Gly Ile Glu Phe Ser His Pro Val Asp Glu
                355                 360                 365

Asn Asn Glu Glu Val Leu Thr Arg Arg Ser Lys Met Val Glu Tyr Lys
        370                 375                 380

Ser His Leu Thr Lys Glu Glu Val Arg Ile Ala Ala Glu Arg Glu
385                 390                 395                 400

Glu Ile Lys Arg Ala Arg Leu Leu Arg Ser Gly Gly Glu Ser Ala Ala
                405                 410                 415

Ala Gln Ile Thr Ser Gly Ser Met Asn Ala Asp Tyr Ala Ala Ser Ala
                420                 425                 430

Gln Leu Glu Leu
        435

<210> SEQ ID NO 10
<211> LENGTH: 389
<212> TYPE: PRT
<213> ORGANISM: Leishmania infantum
<220> FEATURE:
<221> NAME/KEY: SOURCE
<222> LOCATION: 1..389
<223> OTHER INFORMATION: /mol_type="protein"
      /organism="Leishmania infantum"
<220> FEATURE:
<221> NAME/KEY: REGION
<222> LOCATION: 1..389
<223> OTHER INFORMATION: "PFR1 fragment aminoacids 160-548"
<220> FEATURE:
<221> NAME/KEY: PEPTIDE
<222> LOCATION: 6..14
<223> OTHER INFORMATION: "SEQ ID No: 4"
<220> FEATURE:
<221> NAME/KEY: PEPTIDE
<222> LOCATION: 45..53
<223> OTHER INFORMATION: "SEQ ID No: 5"
<220> FEATURE:
<221> NAME/KEY: PEPTIDE
<222> LOCATION: 63..71
<223> OTHER INFORMATION: "SEQ ID No: 6"
<220> FEATURE:
<221> NAME/KEY: PEPTIDE
<222> LOCATION: 214..223
<223> OTHER INFORMATION: "SEQ ID No: 3
```

```
<220> FEATURE:
<221> NAME/KEY: PEPTIDE
<222> LOCATION: 272..280
<223> OTHER INFORMATION: "SEQ ID No: 7"
<220> FEATURE:
<221> NAME/KEY: PEPTIDE
<222> LOCATION: 379..387
<223> OTHER INFORMATION: "SEQ ID no: 8"

<400> SEQUENCE: 10
```

Pro Thr Arg Thr Val Lys Met Met Glu Asp Ile Met Asn Ala Thr Gln
1               5                   10                  15

Ile Gln Asn Ala Leu Ala Ser Thr Asp Asp Gln Met Gln Thr Gln Leu
            20                  25                  30

Ala Gln Leu Glu Lys Thr Asn Glu Ile Gln Asn Val Ala Met His Asp
        35                  40                  45

Gly Glu Thr Gln Val Ala Glu Glu Gln Met Trp Thr Lys Val Gln Leu
    50                  55                  60

Gln Glu Arg Leu Ile Glu Leu Leu Lys Asp Lys Phe Gly Leu Ile Gly
65                  70                  75                  80

Lys Cys Glu Glu Glu Asn Ala Gln Phe Lys Glu Ile Tyr Glu Val Gln
                85                  90                  95

Lys Gln Ala Asn Gln Glu Thr Ser Gln Met Lys Asp Ala Lys Arg Arg
            100                 105                 110

Leu Arg Gln Arg Cys Glu Thr Asp Leu Lys His Ile Gln Asp Ala Ile
        115                 120                 125

Gln Lys Ala Asp Leu Glu Asp Ala Glu Ala Val Lys Arg Tyr Pro Arg
    130                 135                 140

Asn Lys Glu Arg Ser Glu Arg Ala Ile Lys Glu Asn Glu Glu Met Gln
145                 150                 155                 160

Glu Glu Ala Trp Asn Lys Ile Gln Asp Leu Glu Arg Gln Leu Gln Asn
                165                 170                 175

Leu Gly Thr Asp Arg Phe Asp Glu Val Lys Arg Ile Glu Glu Val
            180                 185                 190

Asp Arg Glu Glu Lys Arg Val Glu Asn Ala Gln Phe Leu Glu Ile
        195                 200                 205

Ala Ala Gln His Lys Lys Leu Leu Glu Leu Thr Val Tyr Asn Cys Asp
    210                 215                 220

Leu Ala Met Arg Cys Thr Gly Leu Val Glu Glu Leu Val Ser Glu Gly
225                 230                 235                 240

Cys Ala Gly Val Lys Ala Arg Tyr Asp Lys Thr Asn Gln Asp Leu Ala
                245                 250                 255

Ala Leu Arg Leu Glu Val His Lys Glu His Leu Glu Tyr Phe Arg Met
            260                 265                 270

Leu Tyr Leu Thr Leu Gly Ser Leu Ile Tyr Lys Lys Glu Lys Arg Leu
        275                 280                 285

Glu Glu Ile Asp Arg Asn Ile Arg Leu Ala His Ile Gln Leu Glu Phe
    290                 295                 300

Cys Val Glu Thr Phe Asp Pro Asn Ala Lys Lys His Ala Asp Met Lys
305                 310                 315                 320

Lys Glu Leu Tyr Arg Leu Arg Gln Gly Val Glu Glu Leu Ala Met
                325                 330                 335

Leu Lys Glu Lys Gln Ala Ala Ala Leu Asp Asp Phe Lys Glu Ser Glu
            340                 345                 350

Glu Ala Leu Asp Ala Ala Gly Ile Glu Phe Ser His Pro Val Asp Glu
        355                 360                 365

```
Asn Asn Glu Glu Val Leu Thr Arg Arg Ser Lys Met Val Glu Tyr Lys
        370                 375                 380

Ser His Leu Thr Lys
385

<210> SEQ ID NO 11
<211> LENGTH: 226
<212> TYPE: PRT
<213> ORGANISM: Leishmania infantum
<220> FEATURE:
<221> NAME/KEY: SOURCE
<222> LOCATION: 1..226
<223> OTHER INFORMATION: /mol_type="protein"
      /organism="Leishmania infantum"
<220> FEATURE:
<221> NAME/KEY: REGION
<222> LOCATION: 1..226
<223> OTHER INFORMATION: "PFR1 fragment aminoacids 160-385"
<220> FEATURE:
<221> NAME/KEY: PEPTIDE
<222> LOCATION: 6..14
<223> OTHER INFORMATION: "SEQ ID No: 4"
<220> FEATURE:
<221> NAME/KEY: PEPTIDE
<222> LOCATION: 45..53
<223> OTHER INFORMATION: "SEQ ID No: 5"
<220> FEATURE:
<221> NAME/KEY: PEPTIDE
<222> LOCATION: 63..71
<223> OTHER INFORMATION: "SEQ ID No: 6"
<220> FEATURE:
<221> NAME/KEY: PEPTIDE
<222> LOCATION: 214..223
<223> OTHER INFORMATION: "SEQ ID No: 3"

<400> SEQUENCE: 11

Pro Thr Arg Thr Val Lys Met Met Glu Asp Ile Met Asn Ala Thr Gln
1               5                   10                  15

Ile Gln Asn Ala Leu Ala Ser Thr Asp Asp Gln Met Gln Thr Gln Leu
            20                  25                  30

Ala Gln Leu Glu Lys Thr Asn Glu Ile Gln Asn Val Ala Met His Asp
        35                  40                  45

Gly Glu Thr Gln Val Ala Glu Glu Gln Met Trp Thr Lys Val Gln Leu
    50                  55                  60

Gln Glu Arg Leu Ile Glu Leu Leu Lys Asp Lys Phe Gly Leu Ile Gly
65                  70                  75                  80

Lys Cys Glu Glu Glu Asn Ala Gln Phe Lys Glu Ile Tyr Glu Val Gln
                85                  90                  95

Lys Gln Ala Asn Gln Glu Thr Ser Gln Met Lys Asp Ala Lys Arg Arg
            100                 105                 110

Leu Arg Gln Arg Cys Glu Thr Asp Leu Lys His Ile Gln Asp Ala Ile
        115                 120                 125

Gln Lys Ala Asp Leu Glu Asp Ala Glu Ala Val Lys Arg Tyr Pro Arg
    130                 135                 140

Asn Lys Glu Arg Ser Glu Arg Ala Ile Lys Glu Asn Glu Glu Met Gln
145                 150                 155                 160

Glu Glu Ala Trp Asn Lys Ile Gln Asp Leu Glu Arg Gln Leu Gln Asn
                165                 170                 175

Leu Gly Thr Asp Arg Phe Asp Glu Val Lys Arg Ile Glu Glu Val
            180                 185                 190

Asp Arg Glu Glu Lys Arg Val Glu Asn Ala Gln Phe Leu Glu Ile
        195                 200                 205
```

```
Ala Ala Gln His Lys Lys Leu Leu Glu Leu Thr Val Tyr Asn Cys Asp
            210                 215                 220

Leu Ala
225

<210> SEQ ID NO 12
<211> LENGTH: 595
<212> TYPE: PRT
<213> ORGANISM: Leishmania infantum
<220> FEATURE:
<221> NAME/KEY: SOURCE
<222> LOCATION: 1..595
<223> OTHER INFORMATION: /mol_type="protein"
      /organism="Leishmania infantum"
<220> FEATURE:
<221> NAME/KEY: REGION
<222> LOCATION: 1..595
<223> OTHER INFORMATION: "PFR1 protein aminoacids"
<220> FEATURE:
<221> NAME/KEY: REGION
<222> LOCATION: 160..595
<223> OTHER INFORMATION: "SEQ ID No: 9"
<220> FEATURE:
<221> NAME/KEY: REGION
<222> LOCATION: 160..548
<223> OTHER INFORMATION: "SEQ ID No: 10"
<220> FEATURE:
<221> NAME/KEY: REGION
<222> LOCATION: 160..385
<223> OTHER INFORMATION: "SEQ ID No: 11"
<220> FEATURE:
<221> NAME/KEY: PEPTIDE
<222> LOCATION: 103..113
<223> OTHER INFORMATION: "SEQ ID No: 1"
<220> FEATURE:
<221> NAME/KEY: PEPTIDE
<222> LOCATION: 150..159
<223> OTHER INFORMATION: "SEQ ID No: 2"
<220> FEATURE:
<221> NAME/KEY: PEPTIDE
<222> LOCATION: 165..173
<223> OTHER INFORMATION: "SEQ ID No: 4"
<220> FEATURE:
<221> NAME/KEY: PEPTIDE
<222> LOCATION: 204..212
<223> OTHER INFORMATION: "SEQ ID No: 5"
<220> FEATURE:
<221> NAME/KEY: PEPTIDE
<222> LOCATION: 222..230
<223> OTHER INFORMATION: "SEQ ID No: 6"
<220> FEATURE:
<221> NAME/KEY: PEPTIDE
<222> LOCATION: 373..382
<223> OTHER INFORMATION: "SEQ ID No: 3"
<220> FEATURE:
<221> NAME/KEY: PEPTIDE
<222> LOCATION: 431..440
<223> OTHER INFORMATION: "SEQ ID No: 7"
<220> FEATURE:
<221> NAME/KEY: PEPTIDE
<222> LOCATION: 538..546
<223> OTHER INFORMATION: "SEQ ID No: 8"

<400> SEQUENCE: 12

Met Met Thr Pro Glu Asp Ala Thr Gly Leu Glu Ala Ala Arg Lys Gln
1               5                   10                  15

Lys Ile His Asn Leu Lys Leu Lys Thr Ala Cys Leu Glu Asn Glu Glu
            20                  25                  30

Leu Val Gln Glu Leu His Ile Ser Asp Trp Ser Glu Thr Gln Arg Gln
        35                  40                  45

Lys Leu Arg Gly Ala His Glu Lys Gly Glu Glu Leu Leu Ala Ser Val
    50                  55                  60
```

```
Glu Val Gly Thr Lys Trp Asn Leu Met Glu Ala Tyr Asp Leu Ala Lys
 65                  70                  75                  80

Leu Met Arg Val Cys Gly Leu Glu Met Ser Gln Arg Glu Leu Tyr Arg
                 85                  90                  95

Pro Glu Asp Lys Pro Gln Phe Met Asp Ile Ile Gly Val Lys Lys Val
            100                 105                 110

Leu Gln Asp Leu Arg Gln Asn Arg Asn Lys Thr Arg Val Val Ser Phe
        115                 120                 125

Thr Gln Leu Ile Asp Asn Ser Ile Ala Lys Met Glu Lys Val Glu Glu
    130                 135                 140

Glu Leu Arg Arg Ser Gln Leu Asp Ala Thr Gln Leu Ala Gln Val Pro
145                 150                 155                 160

Thr Arg Thr Val Lys Met Met Glu Asp Ile Met Asn Ala Thr Gln Ile
                165                 170                 175

Gln Asn Ala Leu Ala Ser Thr Asp Asp Gln Met Gln Thr Gln Leu Ala
            180                 185                 190

Gln Leu Glu Lys Thr Asn Glu Ile Gln Asn Val Ala Met His Asp Gly
        195                 200                 205

Glu Thr Gln Val Ala Glu Gln Met Trp Thr Lys Val Gln Leu Gln
    210                 215                 220

Glu Arg Leu Ile Glu Leu Leu Lys Asp Lys Phe Gly Leu Ile Gly Lys
225                 230                 235                 240

Cys Glu Glu Glu Asn Ala Gln Phe Lys Glu Ile Tyr Glu Val Gln Lys
                245                 250                 255

Gln Ala Asn Gln Glu Thr Ser Gln Met Lys Asp Ala Lys Arg Arg Leu
            260                 265                 270

Arg Gln Arg Cys Glu Thr Asp Leu Lys His Ile Gln Asp Ala Ile Gln
        275                 280                 285

Lys Ala Asp Leu Glu Asp Ala Glu Ala Val Lys Arg Tyr Pro Arg Asn
    290                 295                 300

Lys Glu Arg Ser Glu Arg Ala Ile Lys Glu Asn Glu Glu Met Gln Glu
305                 310                 315                 320

Glu Ala Trp Asn Lys Ile Gln Asp Leu Glu Arg Gln Leu Gln Asn Leu
                325                 330                 335

Gly Thr Asp Arg Phe Asp Glu Val Lys Arg Arg Ile Glu Glu Val Asp
            340                 345                 350

Arg Glu Glu Lys Arg Arg Val Glu Asn Ala Gln Phe Leu Glu Ile Ala
        355                 360                 365

Ala Gln His Lys Lys Leu Leu Glu Leu Thr Val Tyr Asn Cys Asp Leu
    370                 375                 380

Ala Met Arg Cys Thr Gly Leu Val Glu Glu Leu Val Ser Glu Gly Cys
385                 390                 395                 400

Ala Gly Val Lys Ala Arg Tyr Asp Lys Thr Asn Gln Asp Leu Ala Ala
                405                 410                 415

Leu Arg Leu Glu Val His Lys Glu His Leu Glu Tyr Phe Arg Met Leu
            420                 425                 430

Tyr Leu Thr Leu Gly Ser Leu Ile Tyr Lys Lys Glu Lys Arg Leu Glu
        435                 440                 445

Glu Ile Asp Arg Asn Ile Arg Leu Ala His Ile Gln Leu Glu Phe Cys
    450                 455                 460

Val Glu Thr Phe Asp Pro Asn Ala Lys Lys His Ala Asp Met Lys Lys
465                 470                 475                 480

Glu Leu Tyr Arg Leu Arg Gln Gly Val Glu Glu Glu Leu Ala Met Leu
```

```
                        485                 490                 495
Lys Glu Lys Gln Ala Ala Leu Asp Asp Phe Lys Glu Ser Glu Glu
                500                 505                 510

Ala Leu Asp Ala Ala Gly Ile Glu Phe Ser His Pro Val Asp Glu Asn
            515                 520                 525

Asn Glu Glu Val Leu Thr Arg Arg Ser Lys Met Val Glu Tyr Lys Ser
        530                 535                 540

His Leu Thr Lys Glu Glu Val Arg Ile Ala Ala Glu Arg Glu Glu
545                 550                 555                 560

Ile Lys Arg Ala Arg Leu Leu Arg Ser Gly Gly Glu Ser Ala Ala Ala
                565                 570                 575

Gln Ile Thr Ser Gly Ser Met Asn Ala Asp Tyr Ala Ala Ser Ala Gln
            580                 585                 590

Leu Glu Leu
        595

<210> SEQ ID NO 13
<211> LENGTH: 680
<212> TYPE: PRT
<213> ORGANISM: Trypanosoma cruzi
<220> FEATURE:
<221> NAME/KEY: SOURCE
<222> LOCATION: 1..680
<223> OTHER INFORMATION: /mol_type="protein"
                        /organism="Trypanosoma cruzi"
<220> FEATURE:
<221> NAME/KEY: REGION
<222> LOCATION: 1..680
<223> OTHER INFORMATION: "HSP70 protein aminoacid sequence"
<220> FEATURE:
<221> NAME/KEY: PEPTIDE
<222> LOCATION: 64..145
<223> OTHER INFORMATION: "Carrier activity fragment"
<220> FEATURE:
<221> NAME/KEY: PEPTIDE
<222> LOCATION: 100..145
<223> OTHER INFORMATION: "Carrier activity fragment"

<400> SEQUENCE: 13

Met Thr Tyr Glu Gly Ala Ile Gly Ile Asp Leu Gly Thr Thr Tyr Ser
1               5                   10                  15

Cys Val Gly Val Trp Gln Asn Glu Arg Val Glu Ile Ile Ala Asn Asp
            20                  25                  30

Gln Gly Asn Arg Thr Thr Pro Ser Tyr Val Ala Phe Thr Asp Ser Glu
        35                  40                  45

Arg Leu Ile Gly Asp Ala Ala Lys Asn Gln Val Ala Met Asn Pro Arg
50                  55                  60

Asn Thr Val Phe Asp Ala Lys Arg Leu Ile Gly Arg Lys Phe Ser Asp
65                  70                  75                  80

Pro Val Val Gln Ser Asp Met Lys His Trp Pro Phe Lys Val Ile Thr
                85                  90                  95

Lys Gly Asp Asp Lys Pro Val Ile Gln Val Gln Phe Arg Gly Glu Thr
            100                 105                 110

Lys Thr Phe Asn Pro Glu Glu Val Ser Ser Met Val Leu Ser Lys Met
        115                 120                 125

Lys Glu Ile Ala Glu Ser Tyr Leu Gly Lys Gln Val Lys Lys Ala Val
    130                 135                 140

Val Thr Val Pro Ala Tyr Phe Asn Asp Ser Gln Arg Gln Ala Thr Lys
145                 150                 155                 160

Asp Ala Gly Thr Ile Ala Gly Leu Glu Val Leu Arg Ile Ile Asn Glu
```

```
                165                 170                 175
Pro Thr Ala Ala Ala Ile Ala Tyr Gly Leu Asp Lys Val Glu Asp Gly
            180                 185                 190
Lys Glu Arg Asn Val Leu Ile Phe Asp Leu Gly Gly Gly Thr Phe Asp
            195                 200                 205
Val Thr Leu Leu Thr Ile Asp Gly Gly Ile Phe Glu Val Lys Ala Thr
            210                 215                 220
Asn Gly Asp Thr His Leu Gly Gly Glu Asp Phe Asp Asn Arg Leu Val
225                 230                 235                 240
Ala His Phe Thr Asp Glu Phe Lys Arg Lys Asn Lys Gly Lys Asp Leu
            245                 250                 255
Ser Thr Asn Leu Arg Ala Leu Arg Arg Leu Arg Thr Ala Cys Glu Arg
            260                 265                 270
Ala Lys Arg Thr Leu Ser Ser Ala Ala Gln Ala Thr Ile Glu Ile Asp
            275                 280                 285
Ala Leu Phe Asp Asn Val Asp Phe Gln Ala Thr Ile Thr Arg Ala Arg
            290                 295                 300
Phe Glu Glu Leu Cys Gly Glu Leu Phe Arg Gly Thr Leu Gln Pro Val
305                 310                 315                 320
Glu Arg Val Leu Gln Asp Ala Lys Met Asp Lys Arg Ala Val His Asp
            325                 330                 335
Val Val Leu Val Gly Gly Ser Thr Arg Ile Pro Lys Val Met Gln Leu
            340                 345                 350
Val Ser Asp Phe Phe Arg Gly Lys Glu Leu Lys Lys Ser Ile Gln Pro
            355                 360                 365
Asp Glu Ala Val Ala Tyr Gly Ala Ala Val Gln Ala Phe Ile Leu Thr
            370                 375                 380
Gly Gly Lys Ser Lys Gln Thr Glu Gly Leu Leu Leu Leu Asp Val Thr
385                 390                 395                 400
Pro Leu Thr Leu Gly Ile Glu Thr Ala Gly Gly Val Met Thr Ser Leu
            405                 410                 415
Ile Lys Arg Asn Thr Thr Ile Pro Thr Lys Lys Ser Gln Ile Phe Ser
            420                 425                 430
Thr Tyr Ala Asp Asn Gln Pro Gly Val His Ile Gln Val Phe Glu Gly
            435                 440                 445
Glu Arg Ala Met Thr Lys Asp Cys His Leu Leu Gly Thr Phe Glu Leu
            450                 455                 460
Ser Gly Ile Pro Pro Pro Arg Gly Val Pro Gln Ile Glu Val Thr
465                 470                 475                 480
Phe Asp Leu Asp Ala Asn Gly Ile Leu Asn Val Ser Ala Glu Glu Lys
            485                 490                 495
Gly Thr Gly Lys Arg Asn Gln Ile Val Leu Thr Asn Asp Lys Gly Arg
            500                 505                 510
Leu Ser Arg Ala Glu Ile Glu Arg Met Val Arg Glu Ala Ala Lys Tyr
            515                 520                 525
Glu Ala Glu Asp Lys Asp Gln Val Arg Gln Ile Asp Ala Lys Asn Gly
            530                 535                 540
Leu Glu Asn Tyr Ala Phe Ser Met Lys Asn Ala Val Asn Asp Pro Asn
545                 550                 555                 560
Val Ala Gly Lys Ile Glu Glu Ala Asp Lys Lys Thr Ile Thr Ser Ala
            565                 570                 575
Val Glu Glu Ala Leu Glu Trp Leu Asn Asn Asn Gln Glu Ala Ser Lys
            580                 585                 590
```

```
Glu Glu Tyr Glu His Arg Gln Lys Glu Leu Glu Asn Leu Cys Thr Pro
        595                 600                 605

Ile Met Thr Asn Met Tyr Gln Gly Met Ala Gly Ala Gly Met Pro Gly
        610                 615                 620

Gly Met Pro Gly Gly Met Pro Gly Gly Met Pro Gly Gly Met Pro Gly
625                 630                 635                 640

Gly Met Pro Gly Gly Met Pro Gly Gly Met Pro Gly Gly Met Pro Gly
                645                 650                 655

Gly Met Pro Gly Gly Met Pro Gly Gly Ala Asn Pro Ser Ser Ser Ser
                660                 665                 670

Gly Pro Glu Val Glu Glu Val Asp
        675                 680
```

CHIMERIC MOLECULE USEFUL IN IMMUNOTHERAPY FOR LEISHMANIASIS, WHICH INCLUDES A FRAGMENT OF THE PFR1 PROTEIN OF LEISHMANIA INFANTUM WITH SPECIFIC IMMUNODOMINANT EPITOPES

CROSS-REFERENCE TO RELATED APPLICATIONS

This application is the United States national phase, under 35 U.S.C. § 371, of International Patent Application No. PCT/ES2012/070541, filed 17 Jul. 2012 and entitled CHIMERIC MOLECULE USEFUL IN IMMUNOTHERAPY FOR LEISHMANIASIS, WHICH INCLUDES A FRAGMENT OF THE PFR1 PROTEIN OF *LEISHMANIA INFANTUM* WITH SPECIFIC IMMUNODOMINANT EPITOPES, which claims the benefit of priority to Spanish Patent Application Serial Number P201131257, filed 21 Jul. 2011 and entitled CHIMERIC MOLECULE USEFUL IN IMMUNOTHERAPY FOR LEISHMANIASIS, WHICH INCLUDES A FRAGMENT OF THE PFR1 PROTEIN OF *LEISHMANIA INFANTUM* WITH SPECIFIC IMMUNODOMINANT EPITOPES, both of which are incorporated herein by reference in their entirety.

SEQUENCE LISTING

A Sequence Listing comprising SEQ ID NOS:1-13, has been provided in computer readable form (.txt) as part of this application, and is incorporated by reference herein in its entirety as part of this application.

The present invention is found within the chemical and pharmaceutical sector, and in the areas of medicine, molecular biology, immunology, parasitology, and veterinary, and refers to an immunological tool for combating leishmaniasis, a disease caused by different species belonging to the genus *Leishmania*.

STATE OF THE ART

The species of the genus *Leishmania*, Protozoan intracellular parasites, belonging to the order Kinetoplastida Trypanosomatidae family, are distributed by tropical and subtropical regions of the world, causing a broad spectrum of clinical symptoms, called leishmaniasis. Sorting by the causative species, leishmaniasis can be classified as cutaneous, mucocutaneous or visceral (in reference to their tissue tropism and the clinical causing symptoms). The incidence of leishmaniasis has increased enormously in recent years, so that it is now endemic in 88 countries across all continents and it is claimed that there are 350 million people at risk of contracting the disease (WHO report, who.int/ctd/html/leisdis.html). It is estimated that worldwide there are about 12 million people affected by leishmaniasis. Accounting 2 million new cases annually, 500,000 are visceral leishmaniasis (VL). This disease is caused by *L. infantum* and *L. donovani* and symptoms of the disease include intermittent fever, anemia, splenomegaly, hepatomegaly, and lymphadenopathy. The outcome of the VL is usually death, caused by a concomitant infection, given the weakness of the immune system of the affected patient. *Leishmania*/HIV co-infection has revealed in recent years as a major health concern in the Mediterranean area countries. In these countries, the main host is the dog, acting as a reservoir of the disease for humans (Alvar et al. 2004 *Adv Parasitol.* 57: 1-88).

Vaccination is the most efficient medical treatment to prevent mortality and morbidity due to infectious agents. Despite this, currently there are very few high-effective vaccines against pathogens against which there is an effective vaccine. Front of the different *Leishmania* species, in recent years, it has been tested the use of antigen vaccines or thereof with disparate results (Kedzierski et al. 2010. *J Glob Infect Dis.* 2 (2): 177-85; Kedzierski et al. 2006. *Parasitology,* 133: 87-112; Requena et al. 2004. *Expert Opin Biol Ther.* 4 (9): 1505-17). However, none of the attempts to obtain a vaccine in humans has been fully satisfactory so far.

Another interesting option in the fight against the disease is therapeutic or, in its absence, the immunochemotherapy. Pasteurized adjuvanted complete parasites have been tested (Convit et al. 2003 *Med Hyg,* 97: 469-72), as well as a mixture of the parasite antigens (Badaro et al. 2006 *J Infect Dis,* 194: 1151-9), but, as in the case of vaccination, any ultimate success has failed (El-On J. 2009. *Isr Med Assoc J,* 11 (10): 623-8).

As it was outlined before, the dog is the main reservoir of the disease, so that several attempts have also been made from the immunological point of view in the fight against this human but also veterinary health problem. In fact, leishmaniasis is a serious parasitic disease in the dog. The most common clinical symptom is loss of hair, especially around the eyes, ears, and nose. In a more advanced stage of the disease the dog lose weight but not appetite and they are common the presence of wounds in the skin, especially on the head and legs, as well as symptoms related to kidney failure. The disease is endemic in large parts of Spain, as well as in most of the countries of the Mediterranean region.

Likewise in humans, there have been made numerous attempts to control the disease from different angles, both prophylactic and immunotherapy, without a completely satisfactory success so far (Alvar et al. 2004. *Adv Parasitol.* 57: 1-88; Reis et al. 2010 *Trends Parasitol.* 26 (7): 341-9).

In any case, either human or canine leishmaniasis, one of the most promising ways of control of leishmaniasis points to the use of DNA vaccines that carry multiple genes coding for specific *leishmania* antigens or chimeric recombinant proteins containing different antigens of the parasite (De Oliveira et al. 2009 *Parasitol Int.* 58 (4): 319-24; Palatnik-de-Sousa, 2008. *Vaccine* 26: 1709-1724).

PFR proteins (Paraflagellar Rod proteins) represent a family of relevant specific antigens of tripanosomatids that are located in the paraflagellar region of these parasites (Fouts et al., 1998 *J Biol Chem,* 273 (34): 21846-21855; Clark et al., 2005. *Parasitol Res.* 96 (5): 312-320). Some members of this family of antigens, PFR1-3 proteins, stand out for their high immunogenicity (Michailowsky et al., *Infect Immun* 71 (6): 3165-3171). Immunization of mice with PFR1 and PFR2 proteins purified from *T. cruzi* induces a Th1 immune response capable of reducing, in experimental infection tests, *T. cruzi* load in the heart tissue of mice immunized and infected with the *T. cruzi* parasite (Morell et al. 2006 *Vaccine,* 24: 7046-7055). These results show that PFR proteins may be suitable candidates for use as vaccines. According to these results, it has been found that lymphocytes CD4+ isolated from mice immunized with PFR are capable of activating parasite-infected macrophages causing the death of the parasite by NO releasing (Wrightsman et al. 2000 *Vaccine* 18 (14): 1419-27, Miller et al. 1997 *J Immunol* 158 (11): 5330-7), and also being able to reduce the level of parasites in blood, in the absence of B cells, but not in the absence of functional CD4+ and CD8+ T lymphocytes as well. From the point of view of gene immunization, different paraflagellar proteins of different kinetoplastids have been studied. The immunogenic and protective capacity of *L. mexicana* PFR2 protein after their inoculation as both DNA and recombinant protein has been demonstrated (Saravia et al. 2005 *Vaccine* 23: 984-995). Immunization of mice with DNA vectors containing the gene that encodes the PFR2 protein of *T. cruzi* alone or fused to the Hsp70 protein of the same pathogen induces high levels of IgG2a type anti-PFR antibodies. However, only the immunization with the chimeric vaccine stimulates the production of IL-12 and IFN-γ, and causes the decrease of IL-4 producing cells, triggering a protective response against *T. cruzi* (Morell et al. 2006 *Vaccine* 24: 7046-7055).

Hsp70 protein belongs to the heat shock proteins (HSP) family, which are highly conserved among the different species (eukaryotes and prokaryotes). They are fundamental in maintaining cellular homeostasis by their role as chaperone (Smith, Whitesell et al. 1998 *Pharmacological Reviews* 50 (4): 493-513). They are very interesting for their ability to activate the immune system, highlighting the Hsp70 family by its immunological versatility. Hsp70 proteins obtained from tumor cells or virus-infected cells are capable of activating CD8+ CTL response both in vivo and in vitro against various expressed antigens in the cells of which the immunogenic protein has been purified from (Srivastava. 2002 *Nat Rev Immunol* 2: 185-194; Wu et al., 2005. *Cancer Res.* 65 (11): 4947-4954). Thus, the extracellular Hsp70 can form complexes with antigenic peptides and activate APCs at the same time. This interaction triggers a cascade of events, gathering processes of peptides cross-presentation to CD8+ restricted MHC I and T CD4+ cells restricted MHC II, secretion of proinflammatory cytokines, and functional and phenotypic maturation of dendritic cells (DCs) (Asea et al. 2000 *Nat Med* 6: 435-442; Basu et al. 2001 *Immunity* 14: 303-313; Harmala et al. 2002 *J Immunol* 169: 5622-5629; Tobian et al. 2004 *J Immunol* 173: 5130-5137).

On in vitro tests carried out in our laboratory, the *Trypanosoma cruzi* Hsp70 protein has shown to have a unique stimulator effect on spleen and ganglion cells of naive mice (Marañón et al., 2000. *Int. Immunol.* 12 (12): 1685-1693), resulting in a quick and intense stimulation of T cells. In addition, this protein is able to induce in vivo and in vitro, against the associated hapten, a mixed immune response (IgG1 and IgG2a) which, interestingly, turns out to be independent of TLR2 and TLR4 receptors (Qazi et al. 2007 *Vaccine* 25 (6): 1096-1103). This *T. cruzi* HSP70 protein has also proven to be capable of triggering a specific response against KMP11 protein in mice when they are immunized with a vector bearing the sequences that encode for both proteins, by activating the production of IgG2a type specific antibodies against KMP11 (Thomas, Olivares et al. 2000 *DNA and Cell Biology* 19 (1): 47-57; Thomas, Olivares et al. 2000 *Acta Tropica* 75 (2): 203-210). Moreover, mice immunized with the KMP11-HSP70 fusion protein, but not those immunized with the isolated KMP11 protein, induce a cytotoxic lymphocyte response against Jurkat-A2/Kb cells expressing the KMP11 protein as well as against those cells loaded with KMP11-derived peptides of proven affinity to A2 molecule. Similar achievements have been obtained using the *Leishmania* genus itself, administering Hsp70 together to the gp63 metalloproteinase of *Leishmania donovani* (Kaur et al. 2011 *Parasite Immunol.* 33 (2): 95-103).

To fight against different species of *Leishmania*, in recent years, vaccines comprising the inactivated whole parasite and/or modified antigens or fragments thereof, as purified as recombinant, have been tested with different results. Thus, according to our own data, none of the previous attempts to obtain a fully successful vaccine for humans or dogs has been achieved so far. Even though chemotherapy currently in use has shown some effectiveness in many cases, it is unable to generate an enough parasite clearance, necessary for a full control and eradication of the disease.

Five years ago, it was carried out the identification of A*0201 molecule-restricted T cell binding epitopes contained in the PFR1 protein, as well as the generation of chimeric molecules (DNA vaccines) formed by the sequences coding for the *L. infantum* PFR1 protein or fragments derived from this protein, for their use both isolated and associated to the HSP70 protein and/or fragments thereof, as a carrier molecule. In addition, it was studied in immunized mice the PFR1-specific immune response induced by the referred chimeric molecules.

There are previous studies in the literature not recommending the use of peptides isolated from the PFR proteins of *T. cruzi* for induction of CTL response. In particular, Wrightsman R. A. et al., published an article in 2002 where various peptides isolated from *T. cruzi* PFR proteins were tested and evaluated whether these peptides were efficiently processed and presented, within the context of a MHC-Class I, in the course of an experimental infection with this parasite and whether they were recognized by cytotoxic T cells (CTLs) in immunized animals (Wrightsman et al. 2002 *Parasite Immunol.* 24 (8): 401-12). In this study, PFR1 epitopes capable of binding to murine HLA class I molecules (H-2 Kb and H-2Db) are identified, but the authors conclude that mice immunization with PFR1 or PFR3 proteins does not induce CTLs against these proteins nor against the identified peptides.

Therefore, in view of the state of the art information, currently there is a need to demonstrate the efficiency of chimeric molecules (DNA and/or recombinant vaccines), formed by the coding sequence of antigenic proteins of *L. infantum* PFR1. The PFR1 protein comprises specific epitopes capable of inducing a CTL response, both isolated and associated with the HSP70 protein and/or fragments thereof, as carrier molecule. At the same time, it is necessary to test its efficacy and safety as prophylactic and therapeutic vaccine against *Leishmania* infection, both in humans and dogs.

BRIEF DESCRIPTION OF THE INVENTION

The present invention represents a useful tool in the fight against animal and human leishmaniasis. It is based on the use of the PFR1 protein-coding nucleotide sequences of *Leishmania infantum* or fragments thereof containing a series of peptides, alone or in conjunction with the Hsp70 protein of *Trypanosoma cruzi*, as well as plasmids containing their genetic encoding sequences. These peptides contained within the PFR1 protein of *L. infantum* correspond to immunodominant epitopes recognized specifically by CD8+T lymphocytes showing cytotoxic capacity, induced by the aforementioned protein used as immunogenicity agent. Where a preferential, the identified epitopes are presented by the human molecule HLA-A*0201. By means of these genetic and protein molecules the present invention provides a cellular and humoral immune response in the host against the protozoan parasite, with capacity for control, significantly, *Leishmania* infection or prevent it. The molecules object of the present invention are relevant for their role in immunotherapy against leishmaniasis used both as a preventive vaccine as therapeutic (isolated or in combination with various chemotherapy). Thus, the use of these molecules represents an industrial advantage over the lack of really effective preventive vaccines against this parasitic disease already in the market along with the difficulties and inconveniences that presents more traditional pharmacological treatments. Although they show some effectiveness in the majority of cases, in many other (especially dogs) do not lead to a complete clearance of the parasite, the whole treatments are quite expensive, they often have many side effects, and there is an increasing occurrence of cases of resistance, among their main setbacks.

DETAILED DESCRIPTION OF THE INVENTION

The present invention claims an isolated nucleotide sequence characterized by encoding the PFR1 protein of *Leishmania infantum* or a fragment thereof. This PFR1 protein or a fragment thereof comprises at least a selected immunodominant epitope between the following group: SEQ ID No: 1, SEQ ID No: 2, SEQ ID No: 3, SEQ ID No: 4, SEQ ID No: 5, SEQ ID No: 6, SEQ ID No: 7 and SEQ ID No: 8, where the immunodominant epitope is able to induce an antigen-specific T cell cytotoxic immune response in an animal, against the kinetoplastids causing the leishmaniasis disease. The immunodominant epitopes are cytotoxic T-lymphocyte activators and they present a high binding affinity for A2 type MHC Class I molecule.

Within the context of the present invention "immunodominant epitope" is considered a fragment peptide capable of being recognized by lymphocyte receptors and of generating an epitope-specific cellular immune response.

In a preferred embodiment of the present invention the expression "animal" refers to a human or a pet, and more preferably a dog.

In a preferred embodiment of the present invention "nucleotide sequence" refers to any nucleotide sequence containing DNA, preferably genomic DNA, synthetic DNA, RNA, in vitro transcribed RNA, messenger RNA, being sense or antisense sequences. Therefore, the present invention refers to these sequences regardless of their obtaining conditions, thus including sequences obtained from a biological sample by cloning or by chemical synthesis or by enzymatic processes.

In a preferred embodiment of the present invention "nucleotide sequence encoding for a protein or a fragment thereof" refers to a nucleotide sequence that is capable, under adequate control of expression by their corresponding regulation elements (promoters, enhancers, transcription sites, etc.), of transcribing and translating one amino acid sequence of the protein of interest or a fragment thereof. The protein of interest as well as the fragments thereof referred to in the present invention is characterized by their amino acids sequence, but they can also be characterized by the cell where they are expressed, their maturation process and the existing environmental conditions during expression.

In a preferred embodiment of the present invention the term "amino acid sequence" refers to a sequence of an oligopeptide, peptide, protein, or their fragments, which are naturally or synthetically produced. As a sequence encoded by a nucleotide sequence is referred within the present invention, the term is not limited to the complete amino acid sequences, or native amino acid sequences associated with the aforementioned protein molecule, it is also referring to the variations that may suffer such native amino acid sequence.

In a particular embodiment, the present invention claims the nucleotide sequence defined above, encoding for the 1-595 amino acids of *Leishmania infantum* PFR1 protein, determined by the SEQ ID No: 12. This fragment encodes the complete protein.

In another particular embodiment, the present invention claims the nucleotide sequence defined above, encoding for the 160-595 amino acids of *Leishmania infantum* PFR1 protein, determined by the SEQ ID No: 9.

In another particular embodiment, the present invention claims the nucleotide sequence defined above, encoding for the 160-548 amino acids of *Leishmania infantum* PFR1 protein, determined by the SEQ ID No: 10.

In another particular embodiment, the present invention claims the nucleotide sequence defined above, encoding for the 160-385 amino acids of *Leishmania infantum* PFR1 protein, determined by the SEQ ID No: 11.

The present invention also protects a chimeric molecule comprising:
(a) a nucleotide sequence defined above, that is preferably fused to
(b) a nucleotide sequence encoding for the Hsp70 protein of *Trypanosoma cruzi*, or fragments thereof;
wherein the chimeric molecule is able to induce an antigen-specific cytotoxic T cell immune response in an animal, against the kinetoplastids causing the leishmaniasis disease.

In a preferred embodiment of the present invention "chimeric molecule" refers to a DNA molecule containing nucleotide sequences from two different species, preferably those species are *Leishmania infantum* and *Trypanosoma cruzi*.

In a particular embodiment, the present invention claims the chimeric molecule defined above, carrying the nucleotide sequence encoding for the Hsp70 protein of *Trypanosoma cruzi*, determined by SEQ ID No: 13, or fragments of the HSP70 with carrier activity.

In another particular embodiment, the present invention claims the chimeric molecule defined above, incorporating at the 3' end of the gene encoding fragment for the PFR1 protein fragment corresponding from 160 to 595 amino acids, characterized by the SEQ ID No: 9, and a nucleotide sequence encoding for the Hsp70 protein of *Trypanosoma cruzi*, determined by the SEQ ID no.: 13 or HSP70 fragments with carrier activity.

In another particular embodiment, the present invention claims the chimeric molecule defined above, incorporating at the 3' end of the gene encoding fragment for the PFR1 protein fragment corresponding from 160 to 548 amino acids, characterized by the SEQ ID No: 10, and a nucleotide sequence encoding for the Hsp70 protein of *Trypanosoma cruzi*, determined by the SEQ ID no.: 13 or HSP70 fragments with carrier activity.

In another particular embodiment, the present invention claims the chimeric molecule defined above, incorporating at the 3' end of the gene encoding fragment for the PFR1 protein fragment corresponding from 160 to 365 amino acids, characterized by the SEQ ID No: 11, and a nucleotide sequence encoding for the Hsp70 protein of *Trypanosoma cruzi*, determined by the SEQ ID no.: 13 or HSP70 fragments with carrier activity.

In another particular embodiment, the present invention claims the chimeric molecule defined above, incorporating at the 3' end of the gene encoding fragment a nucleotide sequence encoding for the Hsp70 protein of *Trypanosoma cruzi*, determined by the SEQ ID no.: 13 or HSP70 fragments with carrier activity.

The present invention also claims a recombinant or expression vector comprising:
(a) a nucleotide sequence defined above, or
(b) a chimeric molecule defined above.

The present invention also claims a recombinant plasmid comprising the vector defined above.

Another embodiment of the present invention claims a composition, preferably pharmaceutical or immunogenic, comprising:
(a) a nucleotide sequence defined above, or
(b) a chimeric molecule defined above.

Another embodiment claimed by the present invention concerns the use of the pharmaceutical or immunogenic composition defined above, for the treatment and/or prevention of kinetoplastids infection that causes leishmaniasis disease in an animal.

Another embodiment claimed by the present invention concerns a method for the manufacture of a preventive or therapeutic vaccines for the treatment and/or prevention of kinetoplastids infection causing the leishmaniasis disease, through the use of the pharmaceutical or immunogenic composition defined above. Such use or method is characterized by comprising the following stages:
a) identifying the encoding sequences of interest, preferably identify at least one nucleotide sequence defined above,
b) amplifying at least one nucleotide sequence identified in a) by PCR using genomic DNA from the kinetoplastid that causes the leishmaniasis disease, and oligonucleotides containing restriction enzymes sites that allow the amplicon direct cloning into prokaryotic and eukaryotic expression vectors after its digestion with these restriction enzymes,
c) cloning at least one nucleotide sequence amplified in b) for the production of the protein encoded by the said nucleotide sequence,
d) purifying at least one of the proteins obtained in c), also known as recombinant proteins (chimeras or not), by affinity chromatography, and
e) producing at least one endotoxin-free DNA vector for a safe inoculation of a preventive or therapeutic vaccine for the treatment and/or prevention of kinetoplastids infection causing the leishmaniasis disease.

Another embodiment claimed by the present invention concerns the use of a nucleotide sequence, a chimeric molecule, a recombinant vector, a recombinant plasmid, or a pharmaceutical or immunogenic composition, as defined above, as markers in methods for controlling the degree of infection of kinetoplastids that cause leishmaniasis disease in an animal.

Preferably, the present invention claims the use of a nucleotide sequence, a chimeric molecule, a recombinant vector, a recombinant plasmid, or a pharmaceutical or immunogenic composition, defined above, to generate a protective immunological memory against the infection of the kinetoplastids causing the leishmaniasis disease in an uninfected animal.

More preferably, the present invention claims the use of a nucleotide sequence, a chimeric molecule, a recombinant vector, a recombinant plasmid, or a pharmaceutical or immunogenic composition, defined above, to clarify or generate partial or total clearance of the kinetoplastids causing the leishmaniasis disease of the tissues in an infected animal.

The present invention has mainly two clear options of immuno-therapeutic applications, a preventive vaccination and its use in immune therapies against infection by *Leishmania*. Likewise, the molecules/products object of the present invention can be used in the form of recombinant proteins, as DNA plasmids (genetic vaccine), or in a combined form.

Thus, a first implementation of the claimed products would be the use of these molecules to generate protective immunological memory against infection by the parasite protozoan mentioned, either in humans or dogs, getting control of the disease in endemic areas (vaccination). Another application would be the use of these molecules as immunotherapy in individuals already infected, in order to enhance the immune response of the host against the parasite and control it. This treatment can be isolated or in combination with other existing chemotherapeutic, chasing the total clearance of the parasite. Thus, activating and modulating the immune response of the host against the parasite and especially by inducing a T cytotoxic antigen-specific response the immune system could eradicate the parasites stationed in tissues, such as bone marrow or spleen that the majority of chemotherapeutic treatments fail to clarify.

Throughout the description and claims the word "comprise" and its variants do not exclude other technical features, additives, components or steps. For experts in the field, other objects, advantages and features of the invention come off as part of the description and as part of the practice of the invention. The following figures and examples are provided for illustration and they are not intended to limit the scope of the present invention.

FIGURE LEGENDS

FIG. 1. Purified PFR-1 recombinant protein was electrophoresed in a 10% SDS-PAGE gel and visualized by coomasie blue staining. MW. Protein molecular weight marker.

Figure 2:
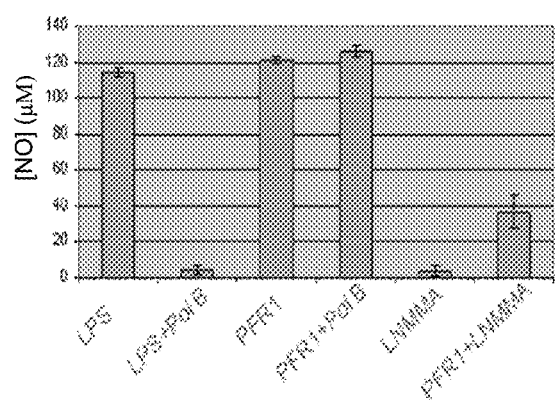

FIG. 2. Measurement of Nitric Oxide (NO) concentration in the supernatant of macrophages culture stimulated with lipopolysaccharide (LPS); lipopolysaccharide+polymyxin B (LPS+PolB); purified PFR-1 protein (PFR-1); purified PFR-1 protein+polymyxin B (PFR1+PolB); L-NG-monomethyl arginine citrate (LNMMA); purified PFR-1 protein+L-NG-monomethyl arginine citrate (PFR1+LNMMA). Concentration is expressed in μmol/liter.

Figures 3A, 3B, 3C:
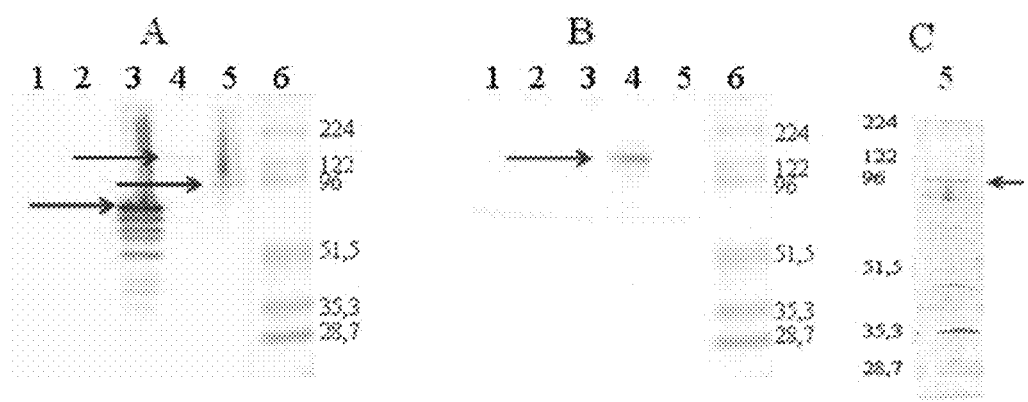

FIGS. 3A to 3C. Western blot analysis of PFR-1 and PFR1-Hsp70 protein expression in COS-7 cells transfected with the pCMV4 empty vector (lane 2) and pCMV4 PFR1 (lane 3); pCMV4 PFR1-Hsp70 (lane 4) and pCMV4 PFR1-Th70 (lane 5) constructs. No transfected cells are used as control (lane 1). Proteinmolecular weight marker (Lane 6). Poly clonal antibody against LiPFR1 (FIG. 3A), TcHsp70 (FIGS. 3B and 3C).

Figure 4A:
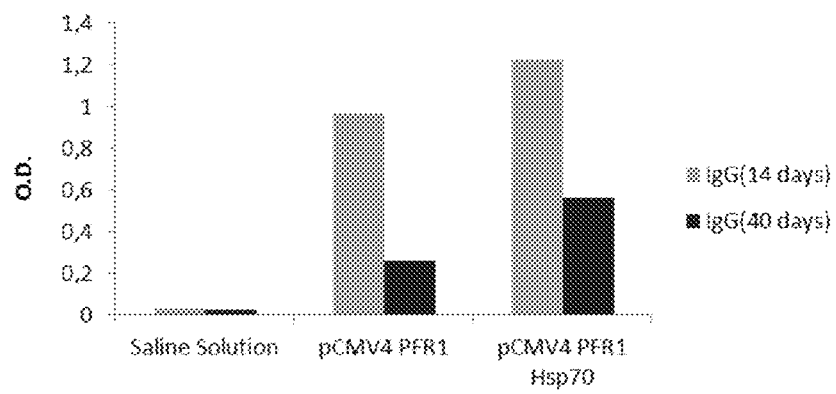
Figure 4B:
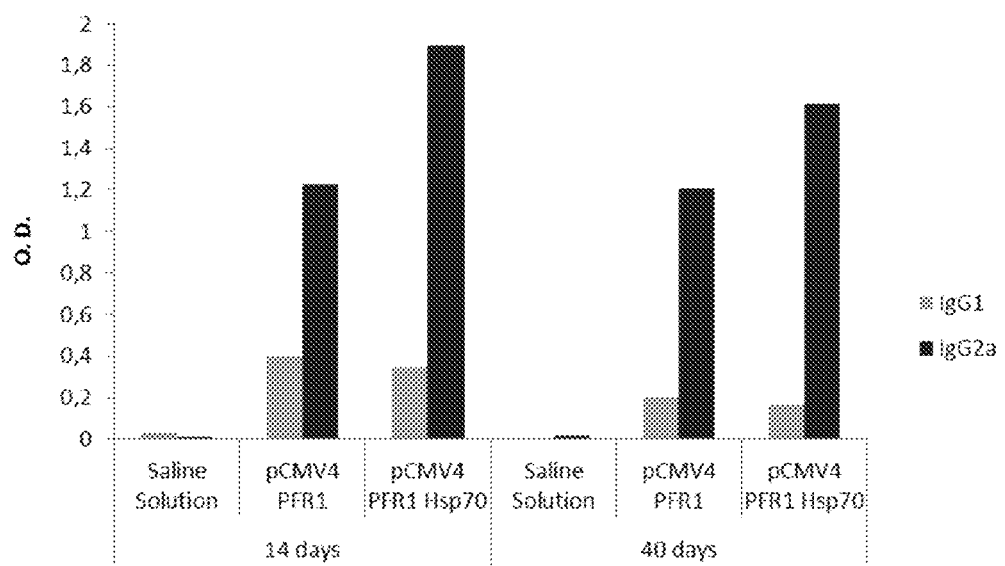

FIGS. 4A to 4B. FIG. 4A. IgG antibody level against PFR-1 recombinant protein in sera from mice inoculated with saline solution and immunized with pCMV4 PFR-1 and pCMV4 PFR1Hsp70 vectors, 14 (grey Bars) and 40 days (black bars) after the fourth immunization. FIG. 4B. Level of IgG1 (grey bars) and IgG2a (black bars) antibodies specific of the PFR-1 recombinant protein detected in the immunized mice referred in FIG. 4A at 14 and 40 days post fourth immunization. Bars represent the mean value of optical density of each group.

FIGS. 5A to 5D. Antibody level against *Leishmania* soluble antigens (SLA, FIGS. 5A, 5B and 5C) and PFR1 recombinant protein (FIG. 5D) in sera from C57BL/6 mice inoculated with saline solution (SS) and, pCMV4 plasmid (pCMV4) or immunized with pCMV4 PFR-1 (PFR1), pCMV4 PFR-1-Hsp70 (70c) and pCMV4 PFR-1 truncated Hsp70 (70t) recombinant vectors, 14 and 21 days after challenge with *Leishmania infantum* infective promastigotes. Bars represent the mean of optical density of each group.

Figure 6:
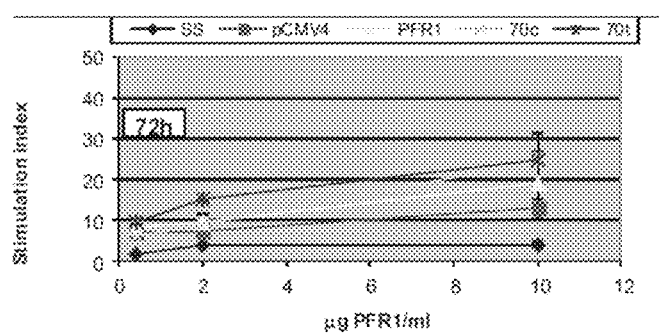

FIG. 6. Lymphoproliferative response to PFR-1 protein in mice inoculated with saline solution (SS) and pCMV4 empty vector (pCMV4) and immunized with pCMV4-PFR1 (PFR1), pCMV4 PFR1-HSP70 (70c) and pCMV4 PFR1-Truncated Hsp70 (70t). Stimulation index was calculated as [(arithmetic mean of cpm (stimulated culture)–arithmetic mean of cpm (control culture))/arithmetic mean of cpm]. The results represent the mean and standard deviation of three independent immunization experiments.

Figure 7:
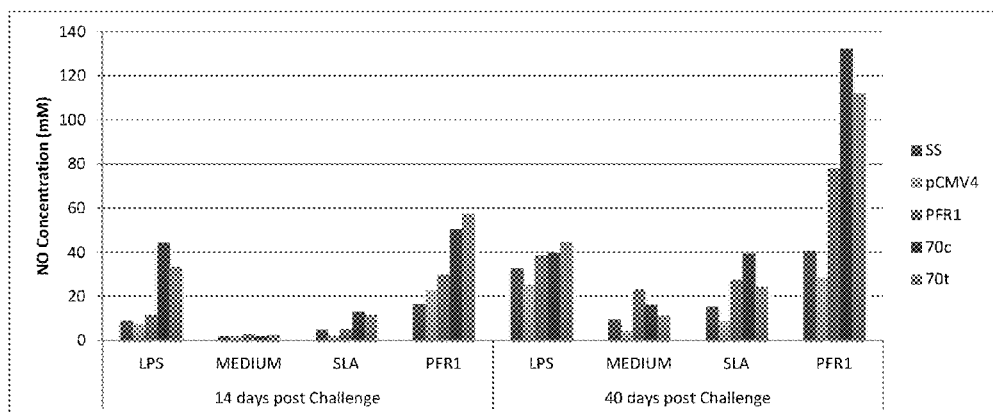

FIG. 7. Nitric Oxide production (NO) by peritoneal macrophages from immunized C57BL/6 mice inoculated with saline solution (SS) and pCMV4 empty vector (pCMV4) or immunized with pCMV4 PFR1 (PFR1), pCMV4 PFR1-Hsp70 (70c) and pCMV4 PFR1-truncated Hsp70 (70t) constructs after *Leishmania infantum* challenge in response to lipopolysaccharide (LPS), culture media (Medium), *Leishmania* soluble antigens (SLA) and PFR1 recombinant protein.

Figure 8:
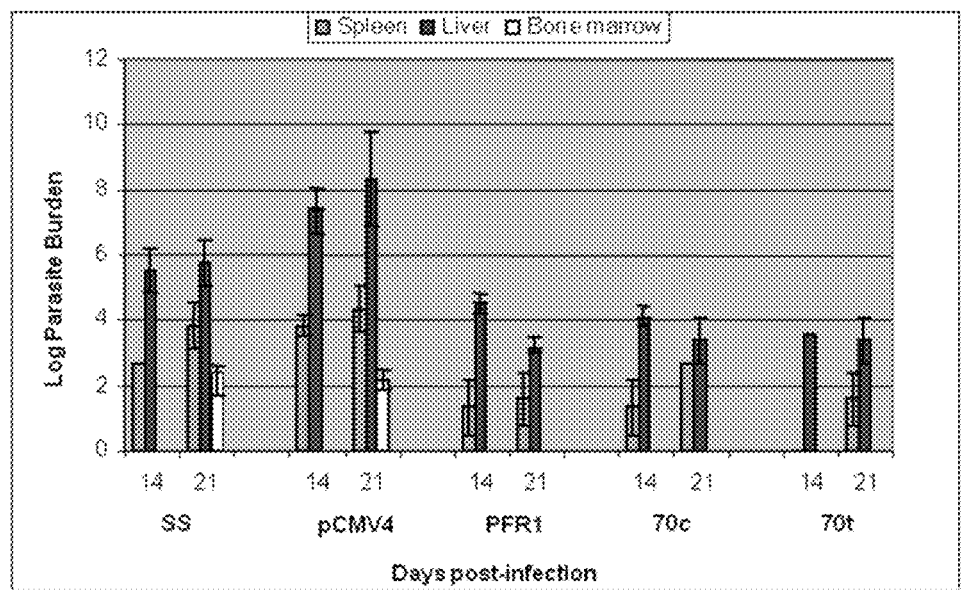

FIG. 8. Parasite burden in spleen, liver and bone marrow from mice inoculated with saline solution (SS) and empty vector pCMV4 (pCMV4) or immunized with pCMV4 PFR1 (PFR1), pCMV4 PFR1-Hsp70 (70c) and pCMV4 PFR1-truncated Hsp70 (70t) recombinant vectors at 14 and 21 days post challenged with *Leishmania infantum* infective promastigotes.

Figure 9:
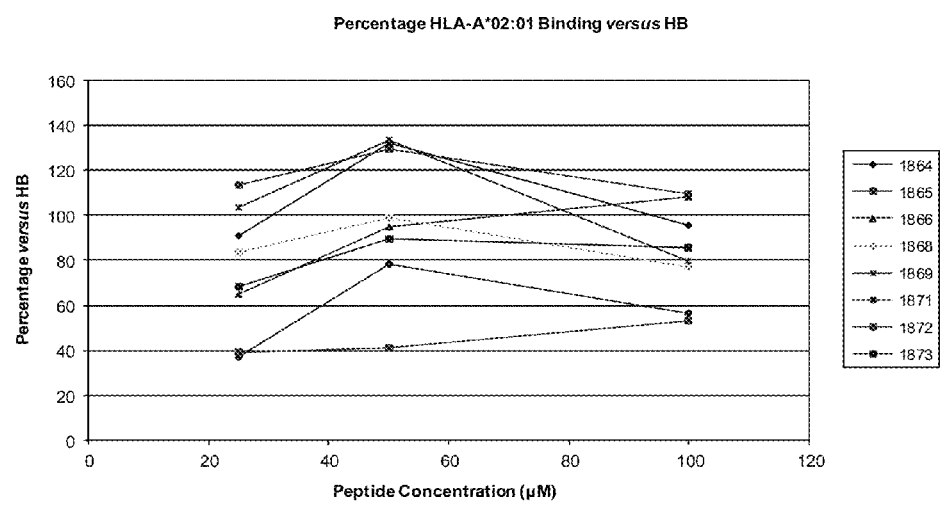

FIG. 9. Binding assay of HLA*02:01-restricted PFR1-derived peptides to TAP-deficient T2 cells. Percentage of maximal complex stabilization was calculated with the HB-ENV$_{334-342}$ peptide fluorescence index as a reference. The binding of each peptide was determined at different concentrations of each peptide.

FIG. 10. Cytotoxic activity of the CD8$^+$ T lymphocytes specific for the eight selected PFR1 peptides evaluated by the secretion of GzB through ELISPOT in splenocytes from B6-A2/K$^b$ mice inoculated with saline solution (SS) or immunized with pCMV4 PFR1 (PFR1) or pCMV4 PFR1-Hsp70 (PFR1-HSP70) recombinant vectors. Spots were visualized using a KS ELISPOT device (Zeiss). Only large spots with fuzzy borders were scored as spot-forming cells (SFC). Responses were considered significant if (i) a minimum of 150 SFC/106 splenocytes were detected after subtraction of the negative control (splenocytes without peptide), and additionally, (ii) the response was at least over two fold the negative control.

FIG. 11. Cytotoxic activity of the CD8$^+$ T lymphocytes specific for the eight selected PFR1 peptides evaluated by the secretion of GzB through ELISPOT in splenocytes from B6-A2/Kb mice infected with *Leishmania infantum* infective promastigotes. Non-inoculated animals were used as control. Spots were visualized using a KS ELISPOT device (Zeiss). Only large spots with fuzzy borders were scored as spot-forming cells (SFC). Responses were considered significant if (i) a minimum of 250 SFC/106 splenocytes were detected after subtraction of the negative control (splenocytes without peptide), and additionally, (ii) the response was at least over two fold the negative control.

FIG. 12. Cytotoxic activity of the CD8+ T lymphocytes specific for the eight selected PFR1 peptides evaluated by the secretion of GzB through ELISPOT in hepatocytes from B6-A2/Kb mice infected with *Leishmania infantum* infective promastigotes. Non-inoculated animals were used as control. Spots were visualized using a KS ELISPOT device (Zeiss). Only large spots with fuzzy borders were scored as spot-forming cells (SFC). Responses were considered significant if (i) a minimum of 75 SFC/106 hepatocytes detected after subtraction of the negative control (hepatocytes without peptide), and additionally, (ii) the response was at least over two fold the negative control.

FIG. 13. The prediction of potential HLA-A*02:01 ligands contained in *L. Infantum* PFR1 protein was carried out through the screening of the deduced amino acid sequence of PFR1 gene using three HLA-A2-binding affinity algorithms: SYPFEITHI www.syfpeithi.de), RANKPEP (immunax.dfci.harvard.edu/Tools/rankpep. html) and BIMAS (theoretical half-time dissociation, www.bimas.cit.nih.gov/molbio/hla_bind/).

Figure 14A:
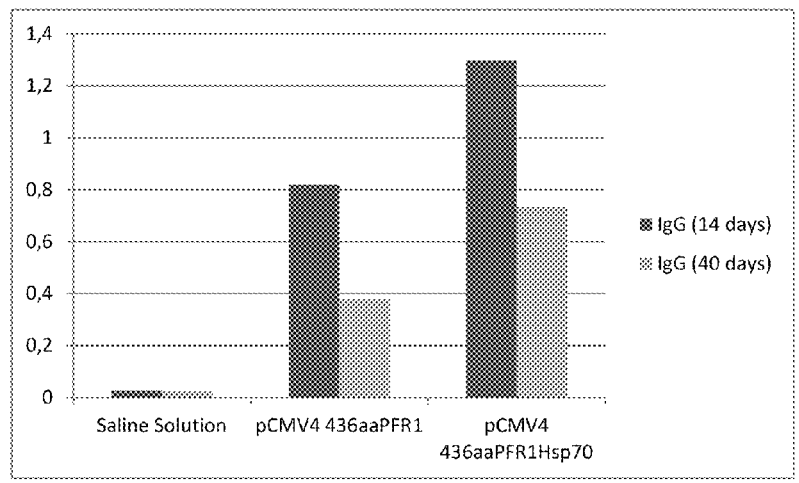
Figure 14B:
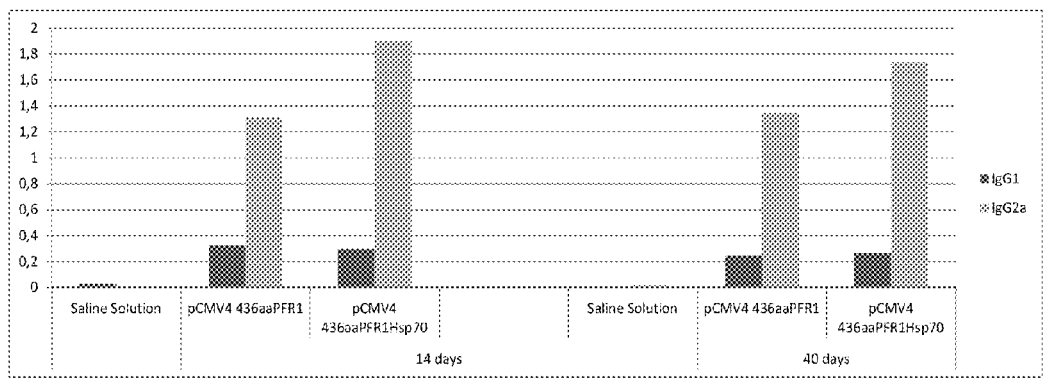

FIGS. 14A to 14B. FIG. 14A. IgG antibody level against PFR1 recombinant protein in sera from mice inoculated with saline solution and immunized with pCMV4 436aaPFR1 and pCMV4 436aaPFR1Hsp70 vectors, 14 (black Bars) and 40 days (grey bars) after the fourth immunization. FIG. 14B. Level of IgG1 (black bars) and IgG2a (grey bars) antibodies specific of the PFR-1 recombinant protein detected in the immunized mice referred in FIG. 14A at 14 and 40 days post fourth immunization. Bars represent the mean value of optical density of each group.

Figures 15, 16:
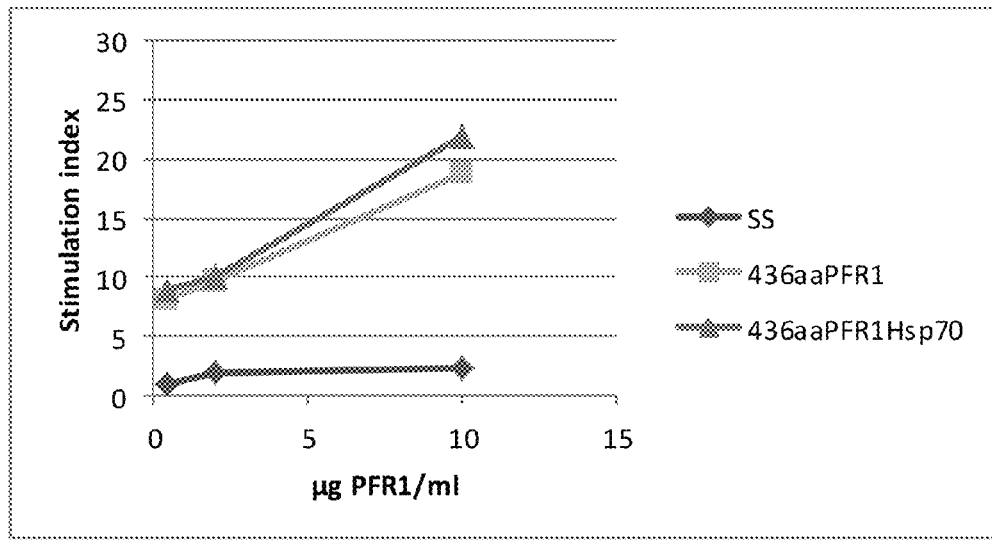

FIG. 15. Lymphoproliferative response to PFR-1 protein in mice inoculated with saline solution (SS) or immunized with pCMV4 436aaPFR1 (436aaPFR1) and pCMV4 436aa PFR1-HSP70 (436aa PFR1 HSP70). Stimulation index was calculated as [(arithmetic mean of cpm (stimulated culture)–arithmetic mean of cpm (control culture))/arithmetic mean of cpm]. The results represent the mean and standard deviation of three independent immunization experiments.

FIG. 16. Cytotoxic activity of the CD8+ T lymphocytes specific for the eight selected PFR1 peptides evaluated by the secretion of GzB through ELISPOT in splenocytes from B6-A2/Kb mice inoculated with saline solution or immunized with pCMV4 436aaPFR1 or pCMV4 436aa PFR1-Hsp70 recombinant vectors. Spots were visualized using a KS ELISPOT device (Zeiss). Only large spots with fuzzy borders were scored as spot-forming cells (SFC). Responses were considered significant if (i) a minimum of 150 SFC/106 splenocytes were detected after subtraction of the negative control (splenocytes without peptide), and additionally, (ii) the response was at least over two fold the negative control.

BIBLIOGRAPHY

1—Alvar et al., 2004. Adv Parasitol. 57: 1-88
2—Kedzierski et al., 2010 J Glob Infect Dis. 2 (2): 177-85
3—Kedzierski et al., 2006 133: 87-112, Parasitology
4—Requena et al., 2004 Expert Opin Biol Ther. 4 (9): 1505-17
5—Convit et al., 2003. Med Hyg, 97: 469-72
6—Badaro et al., 2006 J Infect Dis, 194: 1151-9
7—On j. 2009. ISR Med Assoc J, 11 (10): 623-8
8—Alvar et al., 2004. Adv Parasitol. 57: 1-88
9—Reis et al., 2010. Trends Parasitol. 26 (7): 341-9
10—de Oliveira et al., 2009 Parasitol Int. 58 (4): 319-24
11—Palatnik-de-Sousa, 2008. Vaccine 26: 1709-1724
12—Fouts et al., 1998 J Biol Chem, 273 (34): 21846-21855
13—Clark et al., 2005. Parasitol Res. 96 (5): 312-320
14—Michailowsky et al., Infect Immun 71 (6): 3165-3171
15—Morell et al., 2006 Vaccine, 24: 7046-7055
16—Wrightsman et al., the. 2000 Vaccine 18 (14): 1419-27
17—Miller et al., 1997 J Immunol 158 (11): 5330-7
18—Saravia et al., 2005 Vaccine 23: 984-995
19—Morell et al., 2006 Vaccine 24: 7046-7055

20—Smith, Whitesell et al., 1998 Pharmacological Reviews 50 (4): 493-513
21 Srivastava, 2002 Nat Rev Immunol 2: 185-194
22—Wu et al., 2005. Cancer Res. 65 (11): 4947-4954
23—Asea et al., 2000 Nat Med 6: 435-442
24—Basu et al., 2001 Immunity 14: 303-313
25—Harmala et al., 2002 J Immunol 169: 5622-5629
26—Tobian et al., 2004 J Immunol 173: 5130-5137
27—Marañón et al., 2000. Int. Immunol. 12 (12): 1685-1693
28—Qazi et al., 2007 Vaccine 25 (6): 1096-1103
29—Thomas, Olivares et al., 2000 DNA and Cell Biology 19 (1): 47-57
30—Thomas, Olivares et al., 2000 Acta Tropica 75 (2): 203-210
31—Kaur et al., 2011 Parasite Immunol. 33 (2): 95-103
32—Wrightsman R. A. et al., 2002 Parasite Immunol. 24 (8): 401-12
33—Buffet et al., 1995, Antimicrob. Agents Chemother. 39 (9): 2167-2168

EXAMPLES

The following specific examples that are provided in this patent document are intended to illustrate the nature of the present invention. These examples are only for illustrative purposes and should not be interpreted as limitations to the invention that is claimed here. Therefore, the examples described below illustrate the invention without limiting the field of application of the same.

Example 1

1.1. The PFR1 Protein Induces the Expression of Nitric Oxide (NO)

PFR1 protein of *Leishmania infantum* is encompassed within the family of characteristic proteins of paraflagellar rod proteins from kinetoplastids. In FIG. 1, we show the PFR1 recombinant protein of *L. infantum* expressed in a prokaryotic expression system and purified by affinity chromatography. For this protein we have demonstrated that it has the ability to activate the production of nitric oxide (NO), one of the main mechanisms that the macrophages have to eliminate pathogens that have phagocytosed into alveolar macrophages of nave rat, i.e. without any treatment or previous infection. This activation of nitric oxide production confers to the aforementioned protein a relevant immunological feature because NO favors the clearance of the amastigotes of *Leishmania* that multiply within the host macrophages. In FIG. 2, the values of NO production by these alveolar macrophages are collected by stimulating them with LPS (control) and the PFR1 protein. Interestingly, unlike the one detected for PFR1 protein, the activation observed for LPS is inhibited by the presence of polymyxin B (LPS activity-induced inhibitor), which discards any contamination with LPS from the PFR1 recombinant protein. On the other hand, the addition of L-$N^6$-monomethyl Arginine (LNMMA), an inhibitor of the enzyme nitric oxide synthase, inhibits the NO activation induced by the PFR1 protein, indicating the mechanism of action of this protein. Similar results are obtained by the fusion PFR1-HSP70 protein.

1.2. Expression of PFR1 Protein in Eukaryotic Cells

The determination of the correct expression of the proteins to study in eukaryotic cells is determined by the analysis of COS-7 transfected cells with genes encoding for PFR1 protein and chimeric fusion proteins HSP70-PFR1 and PFR1-H70T cloned into pCMV4 plasmid. The visualization of different proteins is made by Western blots analysis of cells extracts transfected with the respective abovementioned plasmids and induced PFR1-protein polyclonal antibodies. Thus, in FIG. 3 is observed, respectively, the presence of recognition bands with sizes of 70 kDa (corresponding to the PFR1 protein in the cells lane with the pCMV4 PFR1), 140 kDa in the lane of COS-7 cells transfected with the pCMV4 PFR1-Hsp70 plasmid and 96 kDa in the cells lane with the pCMV4 PFR1-Hsp70T plasmid. Cells containing the empty pCMV4 plasmid are not detected.

1.3 Antigen-Specific Humoral Response Induced by the Tested Molecules

As example we show the results obtained after intramuscularly immunization in groups of 12 mice of the C57BL/6 strain, with 100 µg of different plasmids under study, as well as negative controls (empty plasmid and saline solution). Each mouse was immunized 4 times every two weeks. Six weeks after the fourth immunization, six mice in each group were challenged intravenously with 105 infective promastigotes of the JPCM5 (MCAN/s/98/LLM-724) strain of *L. infantum*.
To analyze the humoral response generated in different groups of mice, blood samples were collected two weeks after each immunization and specific antibody measured. The obtained results indicate the presence of anti-PFR1 IgG antibodies 15 days post-second immunization in the group of mice immunized by the isolated PFR1 gene and two weeks after the third immunization in those immunized by the fused HSP70-PFR1 or PFR1-HSP70T genes. FIG. 4 shows the results for each molecule at 14 and −40 days post-fourth immunization. IgG levels registered in sera from mice immunized by the PFR1 gene fused to the HSP70 gene were higher than those detected in mice immunized with the isolated PFR1 gene, peaking within two weeks post-fourth immunization. In all cases the level of anti-PFR1 antibodies slightly descends after six weeks post-fourth immunization. The isotype analysis reflects that generated antibodies show a clear polarization of the response towards the IgG2a isotype (Th1-type immune response). Similar results were obtained for the PPFR1-H70T molecule.
The results obtained in PFR1 protein humoral response assays and total antigens of *Leishmania* (SLA) occurring in mice immunized by the molecules under study and challenged with *L. infantum* are shown in FIG. 5. Analysis of these results indicates that infection with *Leishmania* does not induce significant variation in IgG levels against PFR1 and the same polarization towards the IgG2a isotype is observed prior to the infection.

1.4 Antigen-Specific Cell Response Induced by the Molecules Under Study

Lymphoproliferation tests were carried out three weeks after the fourth immunization. The spleens were extracted in sterile conditions and the obtained splenocytes were cultivated in vitro, with an increasing concentration of the recombinant PFR1 protein (0.4, 2 and 10 µg/ml). In addition, in this assay a mitogen (ConA) and unstimulated splenocytes were included as a positive and negative control, respectively. From the results obtained, shown in FIG. 6, a significant cellular proliferation rate is observed as the recombinant PFR1 is present and, in addition, this stimulation is dose-dependent in the splenocytes from mice immunized by the recombinant testing molecules. Interestingly, this index was significantly higher in the groups receiving the PFR1 gene fused to the HSP70 and HSP70T. The proliferation rate (IE) for the splenocytes from mice immunized with these fusion molecules are approximately 25, while the measured index for splenocytes from mice immunized with the plasmid containing the isolated PFR1 gene is about 20. In both cases, above the controls; mice inoculated with the empty plasmid, IE=13 and saline solution, IE=4. These proliferation rates of splenic cells of mice immunized with the testing molecules remain with similar values after eight weeks post-fourth immunization. In addition, stimulation capacity is maintained after the challenge, noting a maximum of proliferation rate (cellular response) in mice immunized by the isolated PFR1 gene and after stimulating with 2 µg/ml of the PFR1 recombinant protein.

1.5 Expression of Nitric Oxide (NO) in Mice Immunized and Infected by *L. infantum*

As shown in FIG. 7, it can be seen a significant greater ability to produce nitric oxide (NO) in peritoneal macrophages of mice immunized with the testing molecules, especially with the fused ones (PFR1-HSP70 or PFR1-HSP70T) comparing to the control mice, both stimulated and unstimulated. In addition, this NO releasing ability of the mentioned immunized groups of mice increases significantly after stimulation with the recombinant PFR1 protein. On the other hand, such production was significantly higher in the infected mice versus the unchallenged ones.

1.6 Determination of the Capability of Inducing Protection Against *L. infantum* Infection The parasite load was analyzed by limiting dilution (Buffet et al., 1995, *Antimicrob. Agents Chemother.* 39 (9): 2167-2168), in the liver, spleen and bone marrow (target tissues of the parasite), after 14 and 28 days post-infection, showing a summary of the results in FIG. 8. Thus, after 14 days post-infection all groups of mice had parasites in the liver, however, in control groups (ss and pCMV4) the parasite load was significantly higher than the detected in the groups of animals immunized with different testing molecules, showing higher values in at least one order of magnitude. In addition, unlike the control groups, vaccinated mice with the testing molecules do not show an increase in hepatic parasitic load at 28 days post-infection. In fact, mice immunized with PFR1 gene fused to the full HSP70 gene (pPFR1-HSP70), showed and important parasite clearance in the liver. The analysis of the parasite load in spleen shows a similar pattern. Thus, after 14 days post-infection it is observed a significant higher parasite load (at least one order of magnitude) in splenic tissue of control mice (ss and pCMV4) versus vaccinated mice. In fact, mice vaccinated with PFR1 gene fused to the HSP70T gene (pPFR1-H70T) show no parasites in spleen after two weeks post-infection. Regarding bone marrow, only control groups (ss and pCMV4) account parasites, detected just after 28 days post-infection. Interestingly, none of the vaccinated mice presents parasites in this tissue. In summary, all vaccinated groups showed in all analyzed tissues during the infection a significantly lower parasitic load than the control groups (decrease between two to four orders of magnitude), pointing that these molecules confer a high level of protection against *L. infantum* infection, as intravenously administered.

The analysis of the expression pattern of cytokines of splenocytes of vaccinated mice versus control groups (cytometry measures in the supernatant of the cell culture using the Mouse Th1/Th2 Cytokine CBA—BD Biosciences kit) shows the existence of higher levels of TNF-α and IFN-γ and with statistical significance in vaccinated mice with PFR1-HSP70 and PFR1-H70T chimeric constructs, stimulated or unstimulated with rPFR1 and/or SLA, versus the control groups (P<0.01). However, there is not a statistically significant variation among groups regarding IL-2 or IL-4 levels. Likewise, the analysis, after the challenge with *Leishmania*, of the level of the splenic macrophage activation of all the mice groups, problem and control, is measured by the expression pattern of CD80, CD86 and CD40 surface molecules. The results show that after 21 days post-infection the expression of CD86 and CD40 was significantly higher in the vaccinated group with chimeric constructions PFR1-HSP70 and PFR1-H70T versus the control (P<0.01).

1.7 Identification of T CD8+ Epitopes T in the PFR1 Protein of *L. infantum*

The identification of epitopes in the sequence of the PFR1 protein of *L. infantum* able to be recognized by CD8+ T cells and, as a result of activating a cytotoxic antigen-specific response in the host, was carried out trying to identify epitopes capable of binding to MHC-class I HLA. To do this, it was selected, by in silico analyses, different peptides capable of binding to HLA-A*0201 (expressed in the half of the human population), using three programs: SYFPEITHI, RANKPEP, and BIMAS. The deduced sequence of the PFR1 protein of *Leishmania infantum* (gene number: AY702344) was introduced in each of the programs and it was selected the algorithm of binding to HLA-A*0201. The first two programs deliver a score to each peptide based on its theoretical affinity with the HLA molecule. On the other hand BIMAS scores the stability of binding with the HLA molecule, focusing on the theoretical binging time. Combining the results, eight theoretical epitopes of high binding affinity to class I HLA molecule were selected and their corresponding peptides were synthesized: SEQ ID No: 1-1864 (FMDIIGVKKV), SEQ ID No: 2-1865 (QLDATQLAQV), SEQ ID No: 3-1866 (KLLELTVYNC), SEQ ID No: 4-1868 (KMMEDIMNA), SEQ ID No: 5-1869 (AMHDGETQV), SEQ ID No: 6-1871 (QLQERLIEL), SEQ ID No: 7-1872 (MLYLTLGSL) and SEQ ID No: 8-1873 (KMVEYKSHL). The FIG. 13, tables 1 and 2, includes scores for the different peptides in the mentioned software.

To determine the binding capacity to the HLA-A*0201 molecule, it was performed binding tests to T2 cells, having a low expression capacity of transport-antigen molecules. The results, shown in FIG. 9, indicate that all the testing peptides performed a good or very good binding affinity to the HLA-A*0201 molecule, being in some cases superior to the HB-ENV$_{334-242}$ peptide affinity used as control, for which a percentage of 100% binding is expected.

The analysis of the effective presentation capacity of these epitopes in the context of an experimental immunization with the testing molecules, took place in C57BL/6-A2/K$^b$ transgenic mice (they were modified to express the product of the chimeric gene HLA-A2.1/Kb, where alpha1 and alpha2 domains are the same as the HLA-A*0201 human molecule and the alpha3 domains, both transmembrane and cytoplasmic corresponding to the H-2K$^b$ murine molecule) immunized intramuscularly with pPFR1 and pPFR1-HSP70 molecules. Mice injected with saline solution (Sigma) were used as negative control. Six weeks after the fourth immunization the splenocytes of the different mice groups were stimulated with the testing peptides in the context of an ELISPOT assay using an anti-granzyme B antibody as probe. The results obtained (FIG. 10) show that five of the peptides gave a positive response to granzyme B (activation of antigen-specific CTLs) in vaccinated mice with the chimeric molecule pPFR1-HSP70 and one in those immunized with the molecule containing the isolated PFR1 gene. These results demonstrate that the above testing molecules are efficiently processed and presented in the context of the MHC-Class I. Furthermore it points that in particular those epitopes for which positive values are obtained are recognized by cytotoxic T lymphocytes (CTLs) of the immunized mice.

The analysis of the capacity to generate cytotoxic response in the course of an experimental infection with *L. infantum* was evaluated in C57BL/6-A2/Kb transgenic mice infected via i.v. with $10^6$ infective promastigotes of *L. infantum* (strain JPCM5). 170 Days after infection mice were sacrificed and their splenocytes or their not-parenchymal liver cells were exposed to the texting peptides in the context of an ELISPOT assay using Granzima B as detector antibody. The results show (FIGS. 11 and 12) that four of the tested peptides gave a positive response to Granzyme B in splenocytes and three of them also in not-parenchymal liver cells. Therefore, these peptides are presented to the CTLs in the course of experimental infection by the parasite. Interestingly, only one out of these four peptides also gave positive response in immunized mice, showing that the antigen presentation differs between immunization with plasmids and the course of the experimental infection.

CONCLUDING REMARKS

Example 1 conclusion: the results show that immunized mice with the testing molecules and subsequently challenged, do not present parasites in bone marrow, while those groups inoculated with the pCMV4empty plasmid or saline control (control) present a high parasite load in the same tissue after 28 days post-infection. In addition, the parasite load in spleen and liver of immunized mice are between two to four orders of magnitude lower than the detected in the control groups (empty pCMV4 plasmid or saline solution). Immunized mice with the pPFR1-H70T molecule and *Leishmania*-infected, do not show parasites in spleen after 14 days post-infection.

Example 2

2.1 Antigen-Specific Humoral Response

As an example, it is shown the results obtained after intramuscularly immunization of 12-mice-groups of the C57BL/6 strain, with 100 μg of the different testing plasmids, as well as the negative controls (mice inoculated with saline solution). In this case, the tested plasmids contain the sequence corresponding to the fragment of the PFR1 protein of *Leishmania infantum* (436 amino acids length) comprised between amino acids 160 and 595 of the PFR1 protein. Each mouse was immunized 4 times every other week.

To analyze the generated humoral response in different groups of mice, blood collection was made two weeks after each immunization and antibody level detection in animal sera was measured. The results indicate that the presence of anti-PFR1 IgG antibodies appears 15 days post-fourth immunization in the immunized group with the isolated 436aaPFR1 gen and two weeks after the third immunization in those which carry fused 436aaPFR1-HSP70 genes. FIG. 14 (A) shows the results for each testing molecule at 14 and 40 days post-fourth immunization. IgG levels in sera from immunized mice with the 436aaPFR1 gen fused to the HSP70 gene were higher than those detected in the group immunized with the isolated 436aaPFR1 gene, with a maximum of antibodies within two weeks post-fourth immunization. In all cases, the level of anti-PFR1 antibodies slightly descends at six weeks post-fourth immunization. Analysis of isotypes (B) shows a clear polarization of the response towards the IgG2a isotype (Th1 type immune response) in released antibodies.

2.2 Antigen-Specific Cell Response

Lymphoproliferation tests were carried out three weeks after the fourth immunization. The spleens were extracted in sterile conditions and the obtained splenocytes were in vitro cultivated in the presence of an increasing concentration of the rPFR1 protein (0.4, 2 and 10 μg/ml). In addition, a mitogen (ConA) and unstimulated splenocytes were included in this assay as a positive and negative control, respectively. From the results obtained, shown in FIG. 15, a significant cellular proliferation rate is observed as the recombinant PFR1 (rPFR1) is present and, in addition, this stimulation is dose-dependent in the splenocytes of mice immunized by the recombinant testing molecules. Interestingly, this index was significantly higher in the groups receiving the PFR1 gene fused to the HSP70 and HSP70T. The proliferation rate (IE) for the splenocytes of mice inoculated with these fusion molecules are approximately 22, while the measured index for splenocytes from mice immunized with the plasmid containing the isolated PFR1 gene is about 18. In both cases, above the controls; saline solution, IE=4. These proliferation rates of splenic cells of mice immunized with the testing molecules remain with similar values after eight weeks post-fourth immunization.

The analysis of the effective presentation capacity of these epitopes in the context of an experimental immunization with the testing molecules, took place in C57BL/6-A2/K$^b$ transgenic mice (they were modified to express the product of the chimeric gene HLA-A2.1/Kb, where alpha1 and alpha2 domains are the same as the HLA-A*0201 human molecule and the alpha3 domains, both transmembrane and cytoplasmic corresponding to the H-2K$^b$ murine molecule) immunized intramuscularly with 436aaPFR1 and 436aaPFR1-HSP70 molecules. Mice injected with saline solution (Sigma) were used as negative control. Six weeks after the fourth immunization the splenocytes of the different mice groups were stimulated with the testing peptides in the context of an ELISPOT assay using an anti-granzyme B antibody as probe. The results obtained (FIG. 16) show that five of the peptides gave a positive response to granzyme B (activation of antigen-specific CTLs) in vaccinated mice with the chimeric molecule 436aaPFR1-HSP70 and one in those immunized with the molecule containing the isolated436aaPFR1 gene. These results demonstrate that the above testing molecules are efficiently processed and presented in the context of the MHC-Class I. Furthermore it points that in particular those epitopes for which positive values are obtained are recognized by cytotoxic T lymphocytes (CTLs) of the immunized mice.

Conclusion Example 2: the results show that the 436 amino acids fragment of the PFR1 protein performs very similarly to the complete protein, getting a similar pattern of immune response (humoral, cellular and cytotoxic). Therefore, since these parameters are those involved in protection against the parasite, we can conclude that this fragment behaves in all terms to study as the complete protein.

The invention claimed is:

1. A method for prevention of kinetoplastid infections that cause leishmaniasis disease in an animal, comprising use of at least one nucleotide sequence selected from the group consisting of:
- a nucleotide sequence coding for the PFR1 protein of *Leishmania infantum* or a fragment thereof comprising at least one immunodominant epitope selected from the epitope group consisting of: SEQ ID No: 1, SEQ ID No: 2, SEQ ID No: 3, SEQ ID No: 4, SEQ ID No: 5, SEQ ID No: 6, SEQ ID No: 7 and SEQ ID No: 8, wherein the immunodominant epitope is able to induce an antigen-specific T cell cytotoxic immune response against the kinetoplastids causing leishmaniasis disease in an animal;
- a nucleotide sequence coding for the 1-595 amino acids of *Leishmania infantum* PFR1 protein, determined by the SEQ ID No: 12, and comprising at least one immunodominant epitope able to induce an antigen-specific T cell cytotoxic immune response against kinetoplastids causing leishmaniasis disease in an animal;
- a nucleotide sequence coding for the 160-595 amino acids of *Leishmania infantum* PFR1 protein, determined by the SEQ ID No: 9, and comprising at least one immunodominant epitope able to induce an antigen-specific T cell cytotoxic immune response against kinetoplastids causing leishmaniasis disease in an animal;
- a nucleotide sequence coding for the 160-548 amino acids of *Leishmania infantum* PFR1 protein, determined by the SEQ ID No: 10, and comprising at least one immunodominant epitope able to induce an antigen-specific T cell cytotoxic immune response against kinetoplastids causing leishmaniasis disease in an animal; and
- a nucleotide sequence coding for the 160-385 amino acids of *Leishmania infantum* PFR1 protein, determined by the SEQ ID No: 11, and comprising at least one immunodominant epitope able to induce an antigen-specific T cell cytotoxic immune response against kinetoplastids causing leishmaniasis disease in an animal.

2. The method of claim 1, wherein the animal is a human or a dog.

3. A method for generating protective immunological memory against the infection of the kinetoplastids causing the leishmaniasis disease in an uninfected animal, comprising use of at least one nucleotide sequence selected from the group consisting of:
- a nucleotide sequence coding for the PFR1 protein of *Leishmania infantum* or a fragment thereof comprising at least one immunodominant epitope selected from the epitope group consisting of: SEQ ID No: 1, SEQ ID No: 2, SEQ ID No: 3, SEQ ID No: 4, SEQ ID No: 5, SEQ ID No: 6, SEQ ID No: 7 and SEQ ID No: 8, wherein the immunodominant epitope is able to induce an antigen-specific T cell cytotoxic immune response against kinetoplastids causing leishmaniasis disease in an animal;
- a nucleotide sequence coding for the 1-595 amino acids of *Leishmania infantum* PFR1 protein, determined by the SEQ ID No: 12, and comprising at least one immunodominant epitope able to induce an antigen-specific T cell cytotoxic immune response against kinetoplastids causing leishmaniasis disease in an animal;
- a nucleotide sequence coding for the 160-595 amino acids of *Leishmania infantum* PFR1 protein, determined by the SEQ ID No: 9, and comprising at least one immunodominant epitope able to induce an antigen-specific T cell cytotoxic immune response against kinetoplastids causing leishmaniasis disease in an animal;
- a nucleotide sequence coding for the 160-548 amino acids of *Leishmania infantum* PFR1 protein, determined by the SEQ ID No: 10, and comprising at least one immunodominant epitope able to induce an antigen-specific T cell cytotoxic immune response against kinetoplastids causing leishmaniasis disease in an animal; and
- a nucleotide sequence coding for the 160-385 amino acids of *Leishmania infantum* PFR1 protein, determined by the SEQ ID No: 11, and comprising at least one immunodominant epitope able to induce an antigen-specific T cell cytotoxic immune response against kinetoplastids causing leishmaniasis disease in an animal.

4. The method of claim 3, wherein the animal is a human or a dog.

* * * * *